US007618804B2

(12) United States Patent
Tabolina et al.

(10) Patent No.: US 7,618,804 B2
(45) Date of Patent: Nov. 17, 2009

(54) METHOD FOR PRODUCING L-AMINO ACID USING BACTERIA BELONGING TO THE GENUS *ESCHERICHIA*

(75) Inventors: Ekaterina Aleksandrovna Tabolina, Moscow (RU); Konstantin Vyacheslavovich Rybak, Moscow (RU); Evgeni Moiseevich Khourges, Moscow (RU); Elvira Borisovna Voroshilova, Moscow (RU); Mikhail Markovich Gusyatiner, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/120,409

(22) Filed: May 14, 2008

(65) Prior Publication Data

US 2008/0261278 A1 Oct. 23, 2008

Related U.S. Application Data

(62) Division of application No. 10/073,293, filed on Feb. 13, 2002, now Pat. No. 7,476,531.

(30) Foreign Application Priority Data

Feb. 13, 2001 (RU) ................ 2001103865
Feb. 26, 2001 (RU) ................ 2001104998
Feb. 26, 2001 (RU) ................ 2001104999
Jun. 28, 2001 (RU) ................ 2001117632
Jun. 28, 2001 (RU) ................ 2001117633

(51) Int. Cl.
*C12N 1/21* (2006.01)
(52) U.S. Cl. .............. 435/252.33; 435/252.8; 435/107; 435/113; 435/115; 435/116
(58) Field of Classification Search ................ None
See application file for complete search history.

(56) References Cited

U.S. PATENT DOCUMENTS

| | | | |
|---|---|---|---|
| 4,278,765 A | 7/1981 | Debabov et al. | |
| 4,430,430 A | 2/1984 | Momose et al. | |
| 4,996,147 A | 2/1991 | Furukawa et al. | |
| 5,017,483 A | 5/1991 | Furukawa et al. | |
| 5,705,371 A | 1/1998 | Debabov et al. | |
| 5,972,663 A | 10/1999 | Winterhalter et al. | |
| 5,989,875 A | 11/1999 | Kojima et al. | |
| 6,040,160 A | 3/2000 | Kojima et al. | |
| 7,138,266 B2 | 11/2006 | Debabov et al. | |
| 7,259,003 B2 | 8/2007 | Livshits et al. | |
| 7,312,058 B2 | 12/2007 | Kashiwagi et al. | |
| 2002/0028490 A1 | 3/2002 | Molenaar et al. | |
| 2003/0148474 A1 | 8/2003 | Gusyatiner et al. | |
| 2005/0214911 A1 | 9/2005 | Marchenko et al. | |
| 2005/0239175 A1 | 10/2005 | Tabolina et al. | |
| 2006/0040365 A1 | 2/2006 | Kozlov et al. | |
| 2006/0088919 A1 | 4/2006 | Rybak et al. | |
| 2006/0141586 A1 | 6/2006 | Rybak et al. | |
| 2006/0160192 A1 | 7/2006 | Rybak et al. | |
| 2006/0286643 A1 | 12/2006 | Sheremet'eva et al. | |
| 2008/0038825 A1 | 2/2008 | Gunji et al. | |

FOREIGN PATENT DOCUMENTS

| | | |
|---|---|---|
| AU | 199719218 | 12/1996 |
| EP | 643135 | 3/1995 |
| EP | 1016710 | 12/1999 |
| EP | 0994190 | 4/2000 |
| EP | 1013765 | 6/2000 |
| EP | 1085087 | 3/2001 |
| JP | 2000-270888 | 10/2000 |
| WO | WO96/41871 | 12/1996 |
| WO | WO00/61723 | 10/2000 |

OTHER PUBLICATIONS

U.S. Appl. No. 60/644,562, filed Jan. 19, 2005, Rybak et al.
U.S. Appl. No. 60/673,807, filed Apr. 22, 2005, Rybak et al.
U.S. Appl. No. 60/693,507, filed Jun. 24, 2005, Rybak et al.
U.S. Appl. No. 60/693,509, filed Jun. 24, 2005, Sheremet'eva et al.
U.S. Appl. No. 60/703,426, filed Jul. 29, 2005, Rybak et al.
U.S. Appl. No. 60/703,444, filed Jul. 29, 2005, Rybak et al.
U.S. Appl. No. 60/714,943, filed Sep. 8, 2005, Filippov et al.
U.S. Appl. No. 60/714,844, filed Sep. 8, 2005, Filippov et al.
U.S. Appl. No. 60/714,848, filed Sep. 8, 2005, Filippov et al.
U.S. Appl. No. 60/714,849, filed Sep. 8, 2005, Filippov et al.
U.S. Appl. No. 60/723,566, filed Oct. 5, 2005, Rybak et al.
U.S. Appl. No. 60/723,923, filed Oct. 6, 2005, Filippov et al.
U.S. Appl. No. 60/723,925, filed Oct. 6, 2005, Rybak et al.
U.S. Appl. No. 60/723,928, filed Oct. 6, 2005, Rybak et al.
U.S. Appl. No. 60/723,929, filed Oct. 6, 2005, Filippov et al.
U.S. Appl. No. 60/735,830, filed Nov. 16, 2005, Filippov et al.
U.S. Appl. No. 60/743,222, filed Feb. 3, 2006, Rybak et al.
U.S. Appl. No. 60/743,223, filed Feb. 3, 2006, Rybak et al.
U.S. Appl. No. 60/743,226, filed Feb. 3, 2006, Rybak et al.
U.S. Appl. No. 60/743,257, filed Feb. 9, 2006, Rybak et al.
U.S. Appl. No. 60/743,258, filed Feb. 9, 2006, Rybak et al.
U.S. Appl. No. 60/806,819, filed Jul. 10, 2006, Rybak et al.
U.S. Appl. No. 60/807,842, filed Jul. 20, 2006, Filippov et al.
U.S. Appl. No. 60/807,843, filed Jul. 20, 2006, Filippov et al.
U.S. Appl. No. 60/807,845, filed Jul. 20, 2006, Filippov et al.
U.S. Appl. No. 60/829,697, filed Oct. 17, 2006, Rybak et al.
U.S. Appl. No. 60/829,706, filed Oct. 17, 2006, Filippov et al.
U.S. Appl. No. 60/829,923, filed Oct. 18, 2006, Filippov et al.
U.S. Appl. No. 60/829,926, filed Oct. 18, 2006, Rybak et al.
U.S. Appl. No. 60/829,926, filed Nov. 24, 2006, Rybak et al.

(Continued)

*Primary Examiner*—Robert B Mondesi
*Assistant Examiner*—Brian J Gangle
(74) *Attorney, Agent, or Firm*—Shelly Guest Cermak; Cermak Kenealy Vaidya & Nakajima LLP

(57) ABSTRACT

There is provided a method for producing L-threonine, L-valine, L-proline, L-leucine, L-methionine and L-arginine using a bacterium belonging to the genus *Escherichia* wherein the L-amino acid productivity of the bacterium is enhanced by enhancing the activities of the proteins coded by the b2682 and b2683 genes, or the protein coded by the b1242 or b3434 gene.

15 Claims, 1 Drawing Sheet

OTHER PUBLICATIONS

U.S. Appl. No. 60/894,996, filed Mar. 15, 2007, Rybak et al.
U.S. Appl. No. 11/761,465, filed Jun. 12, 2007, Livshits et al.
U.S. Appl. No. 11/830,961, filed Jul. 31, 2007, Filippov et al.
U.S. Appl. No. 11/830,974, filed Jul. 31, 2007, Filippov et al.
U.S. Appl. No. 60/954,663, filed Aug. 8, 2007, Filippov et al.
U.S. Appl. No. 60/954,668, filed Aug. 8, 2007, Filippov et al.
U.S. Appl. No. 60/955,968, filed Aug. 15, 2007, Filippov et al.
U.S. Appl. No. 60/956,945, filed Aug. 21, 2007, Filippov et al.
U.S. Appl. No. 11/849,403, filed Sep. 4, 2007, Rybak et al.
U.S. Appl. No. 11/849,415, filed Sep. 4, 2007, Filippov et al.
U.S. Appl. No. 60/972,028, filed Sep. 13, 2007, Filippov et al.
U.S. Appl. No. 11/934,890, filed Nov. 5, 2007, Filippov et al.
U.S. Appl. No. 11/952,297, filed Dec. 7, 2007, Rybak et al.
U.S. Appl. No. 12/173,379, filed Jan. 22, 2008, Rybak et al.
U.S. Appl. No. 12/022,299, filed Jan. 30, 2008, Rybak et al.
U.S. Appl. No. 61/031,834, filed Feb. 27, 2008, Samsonov et al.
U.S. Appl. No. 12/120,404, filed May 14, 2008, Tabolina et al.
Aleshin, et al., "A new family of amino-acid-efflux proteins" TIBS Trends in Biochemical Sciences, Elsevier Publication, Cambridge, EN, vol. 24, No. 4, Apr. 1, 1999, pp. 133-135, XP004214249.
Blattner, et al., "The Complete Genome Sequence of *Escherichia coli* K-12," Science, vol. 277, Sep. 5, 1977, pp. 1453-1462, w/ seq. listing, 6.pp.I.
Database EMBL "Online! Jan. 29, 1997, Database accession No. AE000353, XP002219992, protein P76630, ygaz "abstract".
Database EMBL 'Online! Jan. 29, 1997 Database accession No. AE000353, XP002219993 protein P43667, ygah "abstract".
Database EMBL 'Online! Feb. 1, 1997 Database accession No. D90852 XP002219994, protein P25743, yche "abstract".
Database EMBL 'Online! Jan. 29, 1997, Database accession No. AE000420, XP002219995 protein P46851, yhgn "abstract".
Database UniProt 'Online! May 1, 1992, XP002318622.
Database EMBL, Jan. 29, 1997.
Database DDBJ/EMBL/GenBank[online], Accession No. P76630, <http://www.ncbi.nlm.nih.gov/entrez/viwer.fcgi?31 23142:OLDID:5252163>, published on Feb. 1, 1998, retrieved on Aug. 13, 2007.
Database DDBJ/EMBL/GenBank[online], Accession No. D65048, http://www.ncbi.nlm.nih.gov/entrez/viewer.fcgi?74 66541:OLD05:65295, published on Oct. 8, 1999, retrieved on Aug. 13, 2007.
Haynes et al., Electrophoresis, 19:1862-1871, 1998.
Horng, G., et al., "Simplifying Nested Radicals and Solving Polynomials by Radicals in Minimum Depth," Proceedings 31$^{st}$ Annual Symposium on Foundations of Computer Science, vol. II, Oct. 22-24, 1990; St. Louis, MO, IEEE Computer Society Press, Loa Alamitos, CA, pp. 847-856.
Kramer, R., "Genetic and physiological approaches for the production of amino acids," J. Biotechnol. 1996;45:1-21.
Lomovskaya, O., et al., "EmrR Is a Negative Regulator of the *Escherichia coli* Multidrug Resistance Pump EmrAB," J. Bacteriol. 1995;177(9):2328-2334.
McGuinness et al., Lancet 337:514-517, Mar. 1991.
Skolnick et al., Trends in Biotech. 18:34-39, 2000.
Voet et al., Biochemistry, 2$^{nd}$ ed., John Wiley and Sons, Inc., 1995, p. 124.
Zakataeva, N. P., et al., "The novel transmembrane *Escherichia coli* proteins involved in the amino acid efflux," FEBS Letters 1999;452:228-232.
Search Report for European Patent App. No. 04028876.3, dated Mar. 10, 2005.
Search Report for European Patent App. No. 04028877.1, dated Mar. 4, 2005.
Notice of Reason for Rejection for Japanese Patent App. No. 2002-034760 (Aug. 21, 2007), with English translation thereof.
Daβler, T., et al., "Identification of a major facilitator protein from *Escherichia coli* involved in efflux of metabolites of the cysteine pathway," Mol. Microbiol. 2000;36(5):1101-1112.
DataBase DDBJ/EMBL/GenBank[online], Accession No. AAC74324.
Turner, R. J., et al., "Expression of *Escherichia coli* TehA Gives Resistance to Antiseptics and Disinfectants Similar to That Conferred by Multidrug Resistance Efflux Pumps," Antimicrobial Agents Chemother. 1997;41(2):440-444.
Notice of Reason for Rejection from Japanese Patent App. No. 2007-273965 (Jun. 10, 2008) with partial English translation thereof.
Notice of Reason for Rejection issue in Japanese Patent App. No. 2007-273972 (Jun. 10, 2008) with English translation.
Database DDBJ/EMBL/GenBank [online], Accession No. AAA58232, http://www.ncbi.nlm.nih.gov/entrez/viewer.fcgi?606369:NCBI:1571702 published on Aug. 18, 1999, retrieved on May 29, 2008.
DataBase DDBJ/EMBL/GenBank[online], Accession No. AAC74324, Dec. 1, 2000.
Livshits, V. A., et al., "Identification and characterization of the new gene *rhtA* involved in threonine and homoserine efflux in *Escherichia coli*," Res. In Microbiol. 2003;154:123-135.
Wechsler, J. A., et al., "Antipolarity in the ilv Operon of *Escherichia coli* K-12," J. Bacteriol. 1969;98(3):1179-1194.
Notice of Final Decision of Rejection for Japanese Patent App. No. 2007-273972 (Jul. 28, 2009) with English translation thereof.
Notice of Final Decision of Rejection for Japanese Patent App. No. 2007-273965 (Jul. 28, 2009) with English translation thereof.
Notice of Final Decision of Rejection for Japanese Patent App. No. 2002-034760 (Jul. 28, 2009) with English translation thereof.

Figure 1. Scheme for construction plasmid pΔlacZ
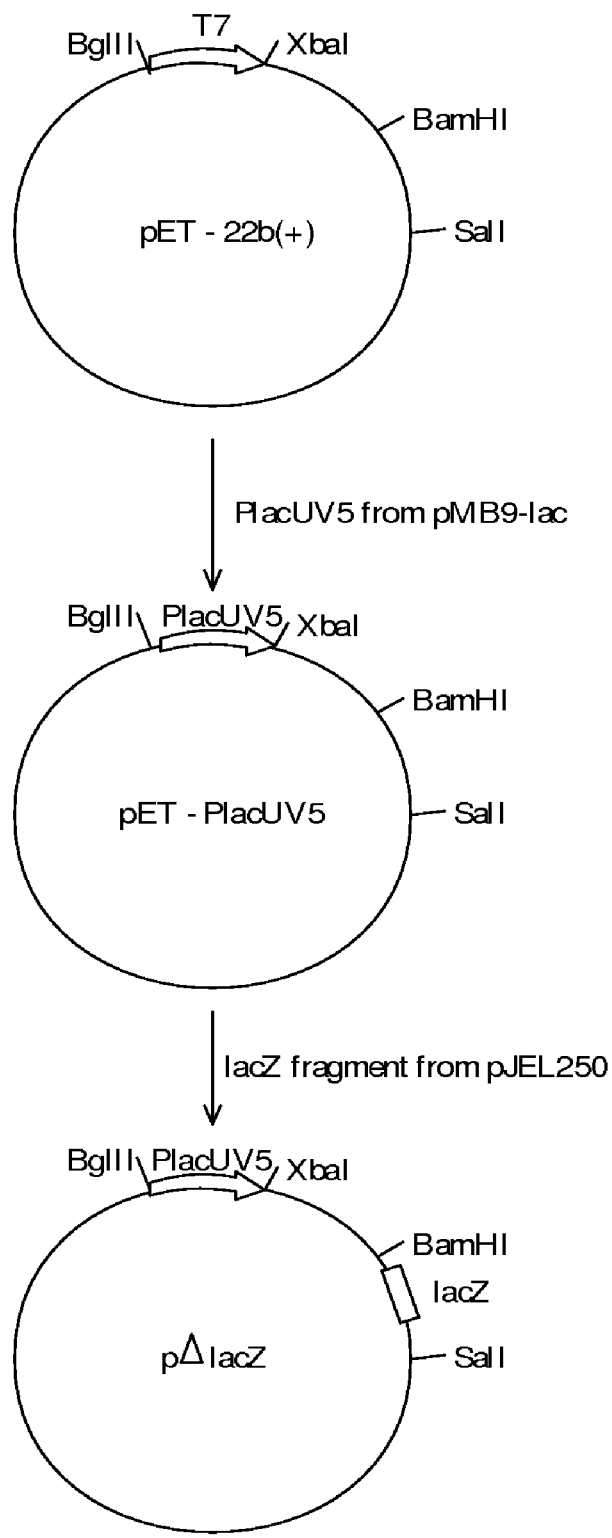

US 7,618,804 B2

METHOD FOR PRODUCING L-AMINO ACID USING BACTERIA BELONGING TO THE GENUS ESCHERICHIA

This application is a divisional under 35 U.S.C. § 120 of U.S. patent application Ser. No. 10/073,293, filed Feb. 13, 2002, issued as U.S. Pat. No. 7,476,531 on Jan. 13, 2009, and claims priority under 35 U.S.C. § 119 to Russian Patent Application No. 2001103865, filed Feb. 13, 2001, Russian Patent Application No. 2001104998, filed Feb. 26, 2001, Russian Patent Application No. 2001104999, filed Feb. 26, 2001, Russian Patent Application No. 2001117632, filed Jun. 28, 2001, Russian Patent Application No. 2001117633, filed Jun. 28, 2001, all of which are incorporated by reference. The Sequence Listing filed electronically herewith is also hereby incorporated by reference in its entirety (File Name: US-145D1_Seq_List_Copy_1; File Size: 21 KB; Date Created: May 14, 2008).

BACKGROUND OF THE INVENTION

1. Field of the Invention

The present invention relates to biotechnology, and specifically to a method for producing L-amino acids by fermentation, and more specifically to genes derived from *Escherichia coli* bacteria. These genes are useful for improving production of L-amino acids, for example, L-threonine, L-valine, L-proline, L-leucine, L-methionine, and L-arginine.

2. Brief Description of the Related Art

Conventionally, L-amino acids are industrially produced by fermentation methods utilizing microorganisms obtained from natural sources or mutants which have been specifically modified to enhance production of the L-amino acids.

Many techniques designed to enhance L-amino acid production have been disclosed, for example, transforming microorganisms with recombinant DNA (see, for example, U.S. Pat. No. 4,278,765). These techniques are based on increasing the activities of the enzymes involved in amino acid biosynthesis and/or desensitizing the enzymes involved in the feedback inhibition by the target L-amino acid (see, for example, Japanese Laid-open application No56-18596 (1981), WO 95/16042, U.S. Pat. Nos. 5,661,012 or 6,040,160).

Alternatively, the secretion of the target L-amino acid can be increased which can enhance the productivity of the strain producing the L-amino acid. Bacteria belonging to the genus *Corynebacterium* in which expression of an L-lysine secretion gene is increased (lysE gene) have been disclosed (WO 9723597A2). In addition, genes coding for the efflux proteins which act to enhance secretion of L-cysteine, L-cystine, N-acetylserine, or thiazolidine derivatives are also disclosed (U.S. Pat. No. 5,972,663).

At present, several *Escherichia coli* genes coding for putative membrane proteins which act to enhance L-amino acid production have been disclosed. The presence of additional copies of the rhtB gene makes bacteria more resistant to L-homoserine and enhances production of L-homoserine, L-threonine, L-alanine, L-valine and L-isoleucine (European patent application EP994190A2). The presence of additional copies of the rhtC gene makes bacteria more resistant to L-homoserine and L-threonine, and enhances production of L-homoserine, L-threonine and L-leucine (European patent application EP1013765A1). The presence of additional copies of the yahN, yeaS, yfiK, and yggA genes enhance production of L-glutamic acid, L-lysine, L-threonine L-alanine, L-histidine, L-proline, L-arginine, L-valine, and L-isoleucine (European patent application EP1016710A2). Even though the complete genome sequence of *Escherichia coli* strain K-12 has been disclosed (Blattner F. R., Plunkett G., Bloch C. A. et al., *Science*, 227, 1453-1474, 1997), the functions of many ORFs remains unknown.

SUMMARY OF THE INVENTION

An aspect of present invention is to enhance the productivity of L-amino acid producing microorganism strains and to provide a method for producing L-amino acids, for example, L-threonine, L-valine, L-proline, L-leucine, L-methionine, and L-arginine, using these strains.

This was achieved by identifying genes coding for proteins which are not involved in the biosynthetic pathways of target L-amino acids, but which enhance production of the target amino acids. An example of such a protein is a membrane protein having L-amino acid excretion activity. Based on the analysis of the complete genome sequence of *Escherichia coli*, proteins with 4 or more putative transmembrane segments (TMS) were selected. As a result, several genes were identified, specifically, b2682, b2683, b1242 and b3434, and studied. The b2682 and b2683 genes are known as putative CDS genes which encode proteins with unknown functions (nucleotide numbers 92 to 829 and 819 to 1154 in GenBank accession AE000353 U00096, respectively). The b2683 gene is also known as ygaH. The b1242 gene is known as a putative CDS which encodes a protein with unknown function (numbers 8432 to 9079 in GenBank accession AE000222 U00096). The b1242 gene is also known as ychE. The b3434 gene also is known as a putative CDS which encodes a protein of unknown function (numbers 1463 to 2056 in GenBank accession AE000420 U00096). The b3434 gene is also known as yhgN.

Also, it has been found that by enhancing the activities of the proteins encoded by the b2682, b2683, b1242, and b3434 genes, the productivity of an L-amino acid producing strain is enhanced.

It is an aspect of the present invention to provide an L-amino acid producing *Escherichia* bacterium, wherein the bacterium has been modified so that the L-amino acid production by the bacterium is enhanced by enhancing activities of proteins selected from the group consisting of:

(A) a protein comprising the amino acid sequence shown in SEQ ID NO:4, (B) a protein comprising the amino acid sequence shown in SEQ ID NO:4, except it includes deletions, substitutions, insertions or additions of one or several amino acids, and which has an activity of making the bacterium have enhanced resistance to the L-amino acids and/or their analogs.

(C) a protein comprising the amino acid sequence shown in SEQ ID NO:6, (D) a protein comprising the amino acid sequence shown in SEQ ID NO:6, except it includes deletions, substitutions, insertions, or additions of one or several amino acids, and which has an activity of making the bacterium have enhanced resistance to the L-amino acids and/or their analogs.

It is a further aspect of the present invention to provide the bacterium as described above, wherein the activities of the proteins defined as (A), (B), (C), or (D) are enhanced by either transformation of the bacterium with a DNA coding for the proteins defined as (A), (B), (C), or (D), or by alteration of expression regulatory sequence of the DNA on the chromosome of the bacterium.

It is a further aspect of the present invention to provide the bacterium as described above, wherein the transformation is performed with a multicopy vector.

It is a further aspect of the present invention to provide a method for producing an L-amino acid comprising cultivating the bacterium as described above in a culture medium and collecting the L-amino acid from the culture medium.

It is a further aspect of the present invention to provide the method as described above, wherein the L-amino acid is L-threonine.

It is a further aspect of the present invention to provide the method as described above, wherein the bacterium has been modified so that the bacterium has enhanced expression of the threonine operon.

It is a further aspect of the present invention to provide the method as described above, wherein the L-amino acid is L-valine.

It is a further aspect of the present invention to provide the method as described above, wherein the bacterium has been modified so that the bacterium has enhanced expression of the ilv operon.

It is a further aspect of the present invention to provide the method as described above, wherein the L-amino acid is L-proline.

It is a further aspect of the present invention to provide the method as described above, wherein the bacterium has been modified so that the bacterium has enhanced expression of genes which encode proteins active in proline biosynthesis.

It is a further aspect of the present invention to provide the method described above, wherein the L-amino acid is L-leucine.

It is a further aspect of the present invention to provide the method as described above, wherein the bacterium has been modified so that the bacterium has enhanced expression of the leu operon.

It is a further aspect of the present invention to provide the method as described above, wherein the L-amino acid is L-methionine.

It is a further aspect of the present invention to provide the method as described above, wherein the bacterium has been modified so that the bacterium has enhanced expression of the met regulon.

It is a further aspect of the present invention to provide an *Escherichia* L-amino acid producing bacterium, wherein the bacterium has been modified so that the L-amino acid production by the bacterium is enhanced by enhancing activities of proteins selected from the group consisting of:

(E) a protein comprising the amino acid sequence shown in SEQ ID NO:12, (F) a protein comprising the amino acid sequence shown in SEQ ID NO: 12, except it includes deletions, substitutions, insertions, or additions of one or several amino acids, and which has an activity of making the bacterium have enhanced resistance to the L-amino acids and/or their analogs, It is a further aspect of the present invention to provide the bacterium as described above, wherein the activities of the proteins defined as (E) or (F) are enhanced either by transformation of the bacterium with a DNA coding for the proteins defined as (E) or (F), or by alteration of an expression regulation sequence of the DNA on the chromosome of the bacterium.

It is a further aspect of the present invention to provide the bacterium as described above, wherein the transformation is performed with a multicopy vector.

It is a further aspect of the present invention to provide a method for producing an L-amino acid comprising cultivating the bacterium as described above in a culture medium and collecting the L-amino acid from the culture medium.

It is a further aspect of the present invention to provide the method as described above, wherein the L-amino acid is L-threonine.

It is a further aspect of the present invention to provide the method as described above, wherein the bacterium has been modified so that the bacterium has enhanced expression of the threonine operon.

It is a further aspect of the present invention to provide the method as described above, wherein the L-amino acid is L-valine.

It is a further aspect of the present invention to provide the method as described above, wherein the bacterium has been modified so that the bacterium has enhanced expression of the ilv operon.

It is a further aspect of the present invention to provide an L-amino acid producing bacterium belonging to the genus *Escherichia*, wherein the bacterium has been modified so that the L-amino acid production by the bacterium is enhanced by enhancing activities of proteins selected from the group consisting of:

(G) a protein comprising the amino acid sequence shown in SEQ ID NO:16, (H) a protein comprising the amino acid shown in SEQ ID NO:16, except it includes deletions, substitutions, insertions, or additions of one or several amino acids, and which has an activity of making the bacterium have enhanced resistance to the L-amino acids and/or its analogs, such as DL-o-methylserine, 6-diazo-5-oxo-L-norleucine and DL-β-hydroxynorvaline, and having enhanced sensitivity to S-(2-aminoethyl)cysteine, It is a further aspect of the invention to provide the bacterium as described above, wherein the activities of the proteins defined as (G) or (H) are enhanced by either transformation of the bacterium with a DNA coding for the proteins defined as (G) or (H), or by alteration of an expression regulation sequence of the DNA on the chromosome of the bacterium.

It is a further aspect of the present invention to provide the bacterium as described above, wherein the transformation is performed with a multicopy vector.

It is a further aspect of the present invention to provide a method for producing an L-amino acid comprising cultivating the bacterium as described in a culture medium and collecting the L-amino acid from the culture medium.

It is a further aspect of the present invention to provide the method as described above, wherein the L-amino acid is L-arginine.

It is a further aspect of the present invention to provide the method as described above, wherein the bacterium has been modified so that the bacterium has enhanced expression of the arginine regulon.

It is a further aspect of the present invention to provide the method as described above, wherein the L-amino acid is L-proline.

It is a further aspect of the present invention to provide the method as described above, wherein the bacterium has been modified so that the bacterium has enhanced expression of genes encoding proteins active in proline biosynthesis.

The method for producing an L-amino acid includes the production of L-threonine, L-valine, L-proline, L-leucine, L-methionine using the appropriate L-amino acid producing bacterium wherein the activities of the proteins comprising the amino acid sequences shown in SEQ ID NO:4 and SEQ ID NO:6 are enhanced.

Furthermore, the method for producing an L-amino acid includes production of L-threonine using an L-threonine producing bacterium wherein the activity of the protein comprising the amino acid sequence shown in SEQ ID NO:12 is enhanced. Also, a method for producing an L-amino acid includes production of L-valine using L-valine producing bacterium wherein the activity of the protein comprising the amino acid sequence shown in SEQ ID NO:12 is enhanced.

Still further, the method for producing an L-amino acid includes the production of L-arginine using an L-arginine producing bacterium wherein the activity of the protein comprising the amino acid sequence shown in SEQ ID NO:16 is enhanced. Also, the method for producing an L-amino acid includes the production of L-proline using an L-proline producing bacterium wherein activities of the comprising amino acid sequence shown in SEQ ID NO:16 are enhanced.

BRIEF DESCRIPTION OF THE DRAWING

FIG. 1 shows the construction of plasmid pΔlacZ.

DETAILED DESCRIPTION OF THE PREFERRED EMBODIMENTS

The present invention will be explained in detail below.

The bacterium of the present invention is an L-amino acid producing bacterium belonging to the genus *Escherichia*, wherein the bacterium has been modified so that the L-amino acid production by the bacterium is enhanced by increasing the activities of the proteins described herein in the bacterium.

"L-amino acid producing bacterium" means a bacterium which has an ability to cause accumulation, that is, produce an L-amino acid when the bacterium is cultured in the medium. The L-amino acid producing ability may be an inherent property of the wild-type bacterium or may be imparted or enhanced by breeding.

The proteins which have increased activity in the bacterium are proteins which increase the production of a target L-amino acid. Specifically, the bacterium is an L-amino acid producing bacterium belonging to the genus *Escherichia* which has enhanced activity of at least one or two of these proteins.

The phrase "enhancing or increasing an activity of a protein" means that the activity per cell is higher than that in a non-modified strain, for example, a wild-type *Esherichia* bacterium. For example, the activity of a protein is increased typically when the number of the protein molecules increases per cell, or when the specific activity per the protein molecule increases, and so forth. Furthermore, a wild-type *Eshcerichia* bacterium may be used for comparison, that is, as a control, and specifically, a wild-type strain of *Escherichia coli*.

Specifically, an example of the bacterium is one which harbors DNA which overexpresses either the b2682 or b2683 gene, and preferably both of these genes, on the chromosomal DNA or on a plasmid in the bacterium. As a result, the bacterium has an enhanced ability to produce an L-amino acid, for example, L-threonine, L-valine, L-proline, L-leucine, and/or L-methionine. Another example of the bacterium is one which harbors DNA which overexpresses the b1242 gene on the chromosomal DNA or on a plasmid in the bacterium, and has an enhanced ability to produce an L-amino acid, for example, L-threonine and/or L-valine. A third example of the bacterium is one which harbors DNA which overexpresses the b3434 gene on the chromosomal DNA or on a plasmid in the bacterium, and has an enhanced ability to produce an L-amino acid, for example, L-arginine and/or L-proline.

The proteins overexpressed by the genes as described above include those shown in SEQ ID NOs:4 and 6, as well as variants of these proteins. The variants include proteins having the amino acid sequences of SEQ ID NOs. 4 and 6, but which include one or more deletions, substitutions, insertions, or additions of one or several amino acids, and which have an activity of making the bacterium have enhanced resistance to the L-amino acids and/or their analogs. The number of amino acids which can be changed differs depending on the position or the type of amino acid residue in the three-dimensional structure of the protein. It may be 1 to 24, preferably 1 to 12, and more preferably 1 to 5 for the protein having the amino acid sequence of SEQ ID NO:4, and 1 to 11, preferably 1 to 7, and more preferably 1 to 5 for the protein having the amino acid sequence of SEQ ID NO:6.

The proteins overexpressed by the genes described above also include those proteins having the amino acid sequence shown in SEQ ID NO:12 and variants thereof. The variants include proteins having the amino acid sequence of SEQ ID NO: 12 but which include one or more deletions, substitutions, insertions, or additions of one or several amino acids, and which have an activity of making the bacterium have enhanced resistance to the L-amino acids and/or their analogs.

The number of amino acids which may be changed differs depending on the position or the type of amino acid residue in the three-dimensional structure of the protein. For the protein of SEQ ID No:12, it may be 1 to 22, preferably 1 to 11, and more preferably 1 to 5. Also, the proteins encoded by the genes described above include those having the amino acid sequence shown in SEQ ID NO. 16 and variants thereof. The variants include proteins having the amino acid sequence of SEQ ID NO: 16, but which include one or more deletions, substitutions, insertions, or additions of one or several amino acids, and which have an activity of making the bacterium have enhanced resistance to the L-amino acids and/or their analogs, such as DL-o-methylserine, 6-diazo-5-oxo-L-norleucine and DL-β-hydroxy-norvaline, and having enhanced sensitivity to S-(2-aminoethyl)cysteine.

Again, the number of amino acids which may be changed differs depending on the position or the type of amino acid residue in the three-dimensional structure of the protein. For the protein having the amino acid sequence of SEQ ID NO:16, it may be 1 to 20, preferably 1 to 10, and more preferably 1 to 5.

Enhanced resistance to L-amino acids and/or their analogs means the bacteria with this enhanced resistance has the ability to grow on a minimal medium containing the L-amino acid or its analog at a concentration which the unmodified strain or the wild-type strain, or the parental strain of the bacterium cannot grow. It can also mean that the bacterium has the ability to grow faster on a medium containing the L-amino acid or its analog than the unmodified strain or the wild-type strain, or the parental strain of the bacterium.

More specifically, the *E. coli* strain has enhanced resistance to the L-amino acid or its analog if the strain forms a colony which is larger than that of the unmodified strain or wild-type strain of *E. coli* after 2-4 days incubation at 37° C. on a plate with solid Adams medium at 37° C. when the strain is cultivated on an agar medium containing the L-amino acid or its analog under appropriate growth conditions. Appropriate growth conditions refer to temperature, pH, air supply, or the optional presence of essential nutrients or the like for the chosen *E. coli* strain.

Examples of L-amino acid analogs include, but are not limited to, 3,4-dihydroproline, DL-thiaisoleucine, DL-o-methylserine, 4-azaleucine, norleucine, L-o-fluorophenylalanine, DL-o-fluorophenylalanine, homoserine, 6-diazo-5-oxo-L-norleucine, and DL-β-hydroxy-norvaline.

The concentration of an L-amino acid or its analog which inhibits the growth of the unmodified strain or the wild-type strain of the bacterium varies significantly, for example, from 0.5 μg/ml for DL-thiaisoleucine to 9600 μg/ml for DL-o-methylserine, depending on the structure of the chosen compound. For example, this concentration is generally 7 to 70 μg/ml, preferably 20 to 25 μg/ml for 3,4-dihydroproline; generally 0.5 to 5 μg/ml, preferably 0.9 to 1.1 for DL-thiaisoleucine; generally 1100 to 9600 μg/ml, preferably 3000 to 3500 for DL-o-methylserine; generally 15 to 150 μg/ml, preferably 40 to 50 μg/ml for 4-azaleucine; generally 150 to 1500 μg/ml, preferably 450 to 550 μg/ml for norleucine; generally 0.6 to 6 μg/ml, preferably 1.5 to 2 μg/ml for L-o-fluorophenylalanine; generally 2 to 20 μg/ml, preferably 5 to 7 μg/ml for DL-o-fluorophenylalanine; and generally 330 to 3300 μg/ml, preferably 900 to 1100 μg/ml for homoserine, generally 5 to 50 μg/ml, preferably 12 to 18 for 6-diazo-5-oxo-L-norleucine, and generally 25 to 250 μg/ml, preferably 70 to 90 μg/ml for DL-β-hydroxy-norvaline Sensitivity to L-amino acids and/or their analogs means that the bacteria are able to grow for longer proliferation times as compared to the unmodified strain or the wild-type strain on a minimal medium containing the L-amino acid or its analog. Alternatively, sensitivity to L-amino acids and/or their analogs means that the bacteria is unable to grow on a minimal medium containing the L-amino acid or its analog at the same concentration that the unmodified strain or the wild-type strain is able to grow. An example of an L-amino acid analog is S-(2-aminoethyl)cysteine. The concentration is generally 0.2 to 2.0 μg/ml, preferably 0.5 to 1.0 μg/ml for S-(2-aminoethyl)cysteine.

The activities of the above proteins in the bacterium can also be enhanced by transforming the bacterium with DNA coding for the protein as described above, or by altering an expression regulatory sequence of the DNA on the chromosome of the bacterium.

The DNA which is used to modify the bacterium codes for a putative membrane protein. More specifically, the DNA codes for a protein which has 4 or more transmembrane segments. This DNA may code for proteins which have L-amino acid excretion activity. More concretely, the DNA is the b2682, b2683, b1242, and b3434 genes. The coding region of the b2682 gene at positions 728-738 and the coding region of the b2683 gene at positions 1-11 are overlapping. Therefore, both genes can be obtained by, for example, PCR using primers having the nucleotide sequence shown in SEQ ID Nos: 1 and 2 as a single PCR product. The b1242 gene can be obtained by, for example, PCR using primers having the nucleotide sequence shown in SEQ ID No: 9 and 10. The b3434 gene can be obtained by, for example, PCR using primers having the nucleotide sequence shown in SEQ ID No: 13 and 14.

Analysis of the complete genome sequence of *Escherichia coli* has allowed for selection of the genes coding for proteins having 4 or more putative TMS. Proteins with known function and transporters described by Paulsen I. T., Sliwinski M. I., Saier M. H. (*J. Mol. Biol.*, 1998, 277, 573) and Linton K. J., Higgins C. F. (*Molecular Microbiology*, 1998, 28(1), 5) were excluded from the group to be screened. As a result of diligent screening among the rest of the genes, several genes coding for putative membrane exporters were chosen. As a result, it was found that the overexpression of the b2682 and b2683 genes, or the b1242 or b3434 genes enhances the L-amino acid production in an L-amino acid producing strain.

The DNA of the present invention includes a DNA coding for the protein which includes one or more deletions, substitutions, insertions, or additions of one or several amino acids in one or more positions in the proteins having the amino acid sequences of SEQ ID NOs. 4 and 6, as long as the activity of the protein is not lost. Although the number of amino acids which can differ depends on the position or the type of the amino acid residue in the three-dimensional structure of the protein, it may be 1 to 24, preferably 1 to 12, and more preferably 1 to 5 for the protein having the amino acid sequence of SEQ ID NO.4, and 1 to 11, preferably 1 to 7, and more preferably 1 to 5 for the protein having the amino acid sequence of SEQ ID NO:6.

Furthermore, the DNA of the present invention includes DNA coding for proteins which include one or more deletions, substitutions, insertions, or additions of one or several amino acids in one or more positions in the protein having the amino acid sequence of SEQ ID NOs: 12 and 16 as long as the activity of the protein is not lost. Although the number of the amino acids which can differ depends on the position or the type of the amino acid residues in the three-dimensional structure of the protein, it may be 1 to 22, preferably 1 to 11, and more preferably 1 to 5 for the protein having the amino acid sequence of SEQ ID NO: 12, and 1 to 20, preferably 1 to 10, and more preferably 1 to 5 for the protein of SEQ ID NO: 16. The DNA coding for the protein variants of the proteins shown in SEQ ID NOs: 4, 6, 12, and 16 may be obtained by, for example, modification of the nucleotide sequence using site-directed mutagenesis so that one or more amino acid residues is deleted, substituted, inserted, or added. The modified DNA can be obtained by conventional methods, for example by treating with reagents and under conditions which result in the generation of mutations. Such reagents include hydroxylamine, N-methyl-N'-nitro-N-nitrosoguanidine, and nitrous acid, and conditions which result in the generation of mutants include the treatment of the bacterium harboring the DNA with UV irradiation.

The DNA of the present invention includes variants which can be found in the different strains and variants of bacteria belonging to the genus *Escherichia* due to natural diversity. Such variant DNA can be obtained by isolating DNA which hybridizes with the b2862, b2683, b1242, or b3434 genes or a part of the genes under the stringent conditions, and which codes for a protein which enhances L-amino acid production. The term "stringent conditions" refers to conditions under which a so-called specific hybrid is formed, and non-specific hybrid is not formed. For example, stringent conditions includes conditions under which DNAs having high homology, for instance DNAs having homology no less than 70% to each other, are hybridized. Alternatively, the stringent conditions are exemplified by the typical conditions used for washing in Southern hybridization, e.g., 60° C., 1×SSC, 0.1% SDS, preferably 0.1×SSC, 0.1% SDS. A partial sequence of the nucleotide sequence of SEQ ID NO: 3 or SEQ ID NO: 5 can be used as a probe for the variants which hybridizes to any of the b2862, b2683, b1242, or b3434 genes. Such a probe may be prepared by PCR using oligonucleotides produced based on the nucleotide sequence of SEQ ID NO: 3, 5, 11 or 15 as primers, and a DNA fragment containing the nucleotide sequence of SEQ ID NO: 3, 5, 11 or 15 as a template. When a DNA fragment of about 300 bp is used as the probe, the conditions of washing for the hybridization are, for example, 50° C., 2×SSC, and 0.1% SDS.

Transformation of a bacterium with DNA coding for a protein means introduction of the DNA into bacterial cell, for example, by conventional methods, which results in increasing expression of the gene coding for the protein and enhancing the activity of the protein in the bacterial cell.

Gene expression can be enhanced by increasing the gene copy number, for example. Also, introducing a gene into a vector that is able to function in the chosen *Escherichia* bacterium increases the copy number of the gene. Multi-copy vectors such as pBR322, pMW119, pUC19, pET22b or the like, are preferably used for this purpose.

Gene expression can also be enhanced by introducing multiple copies of the gene onto the bacterial chromosome by, for example, homologous recombination or the like.

When it is desired to enhance the expression of two or more genes, the genes may be located on the same plasmid, or on different plasmids. It is also acceptable that one of the genes is located on a chromosome, and the other gene is located on a plasmid.

Alternatively, gene expression can be enhanced by altering an expression regulatory sequence of the gene, such as by introducing a mutation in an inherent, i.e. native, expression regulatory sequence of the gene such as a promoter so that the expression of the gene is enhanced (WO00/18935), and/or placing the DNA under the control of a potent promoter. For example, the lac promoter, trp promoter, trc promoter, and $P_L$ promoter of lambda phage are all known as potent promoters. The use of a potent promoter can be combined with increasing the copy number of the gene.

The bacterium of the present invention can be obtained by introducing the aforementioned DNAs into a bacterium which inherently has the ability to produce L-amino acids, or the ability to produce L-amino acids can be imparted to the bacterium. Parent strains for deriving the bacteria of the present invention include L-threonine producing *Escherichia* bacteria such as VL2054 (VKPM B-8067), VNIIGenetika 472T23 (U.S. Pat. No. 5,631,157), VKPM B-3996 (U.S. Pat. Nos. 5,175,107 and 5,976,843), KCCM-10132 (WO009660A1), KCCM-10133 (WO009661A1) or the like; L-valine producing *Escherichia* bacteria such as H-81 (VKPM B-8066), NRRL B-12287 and NRRL B-12288 (U.S. Pat. No. 4,391,907), VKPM B-4411 (U.S. Pat. No. 5,658,766), VKPM B-7707 (European patent application EP1016710A2) or the like; L-proline producing *Escherichia* bacteria such as NRRL B-12403 and NRRL B-12404 (GB2075056), VKPM B-8012 (Russian patent application 2000124295), plasmid mutants described in the patent DE3127361, plasmid mutants described by Bloom F. R. et al. (The 15$^{th}$ Miami winter symposium, 1983, p. 34) or the like; L-leucine producing *Escherichia* bacteria such as H-9070 (FERM BP-4704) and H-9072 (FERM BP-4706) (U.S. Pat. No. 5,744,331), VKPM B-7386 and VKPM B-7388 (RU2140450), W1485atpA401/pMWdAR6, W1485lip2/pMWdAR6 and AJ12631/pMWdAR6 (EP0872547) or the like; L-methionine producing *Escherichia* bacteria such as AJ11539 (NRRL B-12399), AJ11540 (NRRL B-12400), AJ11541 (NRRL B-12401), AJ 11542 (NRRL B-12402) (GB2075055) or the like; L-arginine producing *Escherichia* bacteria such as AJ11531 and AJ11538 (JP56106598A2), AJ11593 (FERM P-5616) and AJ11594 (FERM P-5617) (Japanese Patent Laid-open No. 57-5693) or the like.

The expression of one or more genes which encode proteins involved in the biosynthesis of L-amino acids may also be increased or enhanced. In L-threonine producing bacteria, such genes include the genes of the threonine operon, such as the gene encoding aspartate kinase, or homoserine dehydrogenase which is desensitized to feedback inhibition by L-threonine (Japanese Patent Publication No. 1-29559). For L-valine producing bacteria, such genes include the ilv operon, that is, the ilvGMEDA operon, which does not preferably express threonine deaminase and which has suppressed attenuation (Japanese Patent Laid-Open Publication No. 8-47397). For L-proline producing bacteria, such genes include the proB gene encoding for glutamate kinase which has been desensitized to feedback inhibition by L-proline (DE3127361). For L-leucine producing bacteria, such genes include the leucine operon, that is, the leu operon, which preferably includes a gene coding for isopropylmalate synthase which is desensitized to feedback inhibition by L-leucine (Russian patent application 99114325). For L-methionine producing bacteria, such genes include the methionine regulon. The methionine regulon may have mutated genes coding for proteins which have a decreased activity for repressing amino acid biosynthesis. An example is the metJ gene coding for a L-methionine biosynthesis-relating repressor protein from *E. coli*, which has decreased activity for repressing methionine biosynthesis (JP 2000-157267 A2). Furthermore, another example is the arginine regulon, which preferably includes a gene encoding N-acetylglutamate synthase which is desensitized to feedback inhibition by L-arginine (Rajagopal B. S. et al, Appl. Environ. Microbiol., 1998, v. 64, No. 5, p. 1805-1811).

The method of the present invention includes a method for producing L-threonine, L-valine, L-proline, L-leucine, and/or L-methionine by cultivating the bacteria with enhanced activities of the proteins shown in SEQ ID NOs: 4 and 6 in a culture medium, allowing L-threonine to accumulate in the culture medium, and collecting L-threonine from the culture medium.

The method of the present invention also includes a method for producing L-threonine and/or L-valine by cultivating the bacteria with enhanced activity of the protein shown in SEQ ID NO: 12 in a culture medium, allowing L-threonine to accumulate in the culture medium, and collecting L-threonine from the culture medium.

The method of present invention further includes a method for producing L-arginine and/or L-proline by cultivating the bacteria with enhanced activity of the protein shown in SEQ ID NO: 16 in a culture medium, to allow L-arginine to be produced and accumulated in the culture medium, and collecting L-arginine from the culture medium. Also, the method of present invention includes a method for producing L-proline by cultivating the bacterium of the present invention in a culture medium, to allow L-proline to be produced and accumulated in the culture medium, and collecting L-proline from the culture medium.

The cultivation, collection, and purification of L-amino acids from the medium and the like may be performed in a manner similar to conventional fermentation methods wherein an amino acid is produced using a microorganism. The medium used for culture may be either synthetic or natural, so long as it includes a carbon and nitrogen source, minerals and, if necessary, appropriate amounts of nutrients required by the chosen microorganism for growth. The carbon source may include various carbohydrates such as glucose and sucrose, and various organic acids. Depending on the mode of assimilation of the chosen microorganism, alcohol including ethanol and glycerol may be used. As the nitrogen source, various ammonium salts such as ammonia and ammonium sulfate, other nitrogen compounds such as amines, a natural nitrogen source such as peptone, soybean-hydrolysate and digested fermentative microorganism are used. As minerals, potassium monophosphate, magnesium sulfate, sodium chloride, ferrous sulfate, manganese sulfate, calcium chloride, and the like are used.

The cultivation is performed preferably under aerobic conditions such as a shaking culture, and stirring culture with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to the accumulation of the target L-amino acid in the liquid medium.

After cultivation, solids such as cells can be removed from the liquid medium by centrifugation or membrane filtration, and then the target L-amino acid can be collected and purified by ion-exchange, concentration and crystallization methods.

EXAMPLES

The present invention will be more concretely explained below with reference to the following non-limiting Examples. In the Examples, amino acids are in the L-configuration unless otherwise noted.

Example 1

Cloning of the b2682, b2683, b1242, and b3434 Genes on the Plasmid pΔlacZ

To clone the b2682 and b2683 genes, vector pΔlacZ was used. pΔlacZ is a derivative of the pET-22b(+) vector (Novagen, Madison, Wis., USA). pET-22b(+) was treated by BglII and XbaI and ligated with the polymerase chain reaction (PCR) fragment of plasmid pMB9-lac (Fuller F., Gene, 19, 43-54, 1982) which had been treated with the same restrictases and carried the $P_{lac}$ UV5 promoter. To amplify the $P_{lac}$ UV5 promoter fragment by PCR, primers having the sequences depicted in SEQ ID Nos: 7 and 8 were used. Then, the structural part of the lacZ gene (237 bp without promoter) was cloned into the plasmid using the SalI-BamHI fragment of the plasmid pJEL250 (Dymakova E. et al., Genetika (rus), 35, 2, 181-186, 1999). The scheme for obtaining the pΔlacZ vector is shown in FIG. 1.

The PCR fragment obtained using DNA from E. coli strain TG1 as a template was used as the initial material to clone the E. coli b2682 and b2683 putative reading frames (b2682 and b2683 genes). The primers having the sequences depicted in SEQ ID Nos: 1 and 2 were used to synthesize this PCR fragment. PCR was carried out on "Perkin Elmer GeneAmp PCR System 2400" under the following conditions: 40 sec. at 95° C., 40 sec. at 47° C., 40 sec. at 72° C., 30 cycles. Thus, a 1158 bp linear DNA fragment containing the b2682 and b2683 genes was obtained. This PCR fragment was treated with the XbaI and BamHI restrictases and inserted into the multicopy vector pΔlacZ which had been previously treated with the same restrictases.

The plasmid with the PCR fragment was named pYGAZH, and carried both the b2682 and b2683 genes under the control of the lactose promoter ($P_{lac}$ UV5).

Similarly, the PCR fragment obtained using DNA from E. coli strain TG1 as a template was used as the initial material to clone the E. coli b1242 putative reading frame (b1242 gene). The primers having the sequences depicted in SEQ ID Nos: 9 and 10 were used to synthesize this fragment. The plasmid containing the PCR fragment was named pYCHE and carried the b1242 gene under the control of the lactose promoter ($P_{lac}$ UV5). The initial material for cloning of the E. coli b3434 putative reading frame (b3434 gene) was the PCR fragment, which was obtained using DNA from E. coli strain TG1 as a template. The primers having the sequences depicted in SEQ ID Nos :13 and 14 were used to synthesize this fragment. The plasmid containing the PCR fragment was named pYHGN and carried the b3434 gene under the control of the lactose promoter ($P_{lac}$ UV5).

Example 2

The Influence of the Amplified b2682 and b2683 Genes on the Resistance of E. coli Strain TG1 to Amino Acids and their Analogs E. coli strains TG1(pYGAZH), TG1(pYCHE), and TG1 (pYHGN), as well as a control TG1 strain having a vector without an insertion were grown overnight on LB medium supplemented with ampicillin (100 μg/ml). The night cultures of all the strains were diluted 25 times in fresh LB medium supplemented with ampicillin (100 μg/ml) and IPTG (0.5 mM) and were incubated 2 hours at 37° C. with aeration. The log phase cultures were diluted in a 0.9% solution of NaCl and about 1000 cells were seeded on plates with solid Adams medium supplemented with ampicillin (100 μg/ml), IPTG (0.5 mM), and an amino acid or its analog. After 2-4 days incubation at 37° C., the differences in colony size or colony number between the TG1 cells with the hybrid plasmids and the control TG1 cells were observed. The results of these experiments are presented in Table 1.

TABLE 1

| Inhibitors | Concentration in media, μg/ml | Effect on the growth of TG1 strain having plasmid | | |
|---|---|---|---|---|
| | | pYGAZH | pYCHE | pYHGN |
| Proline | 30000 | No | No | No |
| 3,4-Dihydroproline | 23 | R | No | No |
| Isoleucine | 18000 | No | No | No |
| DL-Thiaisoleucine | 1 | R | No | No |
| o-Methylthreonine | 6 | No | No | No |
| L-Serine | 2800 | No | No | No |
| DL-Serine | 3600 | No | No | No |
| DL-Serine hydroxamate | 140 | No | No | No |
| DL-o-Methylserine | 3200 | R | R | R |
| 4-Azaleucine | 45 | R | No | No |
| 6-Diazo-5-oxo-L-norleucine | 15 | No | No | R |
| Valine | 7 | R | No | No |
| Methionine | 38000 | No | No | No |
| Norleucine | 500 | R | No | No |
| Cysteine | 1600 | No | No | No |
| Homoserine | 1000 | No | R | No |
| DL-β-Hydroxy-norvaline | 80 | No | No | R |
| L-Aspartic acid β-hydroxamate | 100 | No | No | No |
| Arginine | 4300 | No | No | No |
| Lysine | 5000 | No | No | No |
| S-(2-Aminoethyl)cysteine | 0.75 | No | No | S |
| Histidine | 3000 | No | No | No |
| L-Histidine hydroxamate | 200 | No | No | No |
| DL-1,2,4-Triazole-3-alanine | 80 | No | No | No |
| Phenylalanine | 13000 | No | No | No |
| p-Fluorophenylalanine | 6 | No | No | No |
| L-o-Fluorophenylalanine | 1.7 | R | No | No |
| DL-o-Fluorophenylalanine | 6 | R | No | No |
| Tryptophan | 12500 | No | No | No |
| DL-4-Fluorotryptophan | 0.1 | No | No | No |
| 4-Methyltryptophan | 0.25 | No | No | No |
| 7-Methyltryptophan | 100 | No | No | No |
| DL-a-Methyltryptophan | 400 | No | No | No |
| m-Fluoro-DL-tyrosine | 0.5 | No | No | No |

No - no differences compared to the control strain
R - more colonies or increased colony size
S - less colonies or decreased colony size compared to the control strain

Example 3

Production of Threonine by Cells Having Plasmid pYGAZH

The threonine producing strain VL2054 was transformed with the plasmid pYGAZH which contains the b2682 and b2683 genes under the control of $P_{lac}$ UV5 promoter. The resulting strain was named VL2054(pYGAZH). The VL2054 strain is a derivative of the VKPM B-3996 strain and carries on its chromosome:

a) the integrated threonine operon under the control of the PR promoter, b) the wild-type rhtA gene, c) the inactivated chromosomal gene encoding transhydrogenase (tdh gene) and the inactivated kanamycin resistant gene (kan) in the Tn5 (tdh::Tn5, $Kan^S$), d) the mutation $ilvA_{442}$.

The VL2054 strain was deposited in the Russian National Collection of Industrial Microorganisms (VKPM) (Russia 113545, Moscow, 1 Dorozhny proezd, 1) on Jan. 30, 2001 under accession number VKPM B-8067, and converted to an international deposit based on the Budapest Treaty on Feb. 1, 2002.

5 colonies of each VL2054 strain, the control strain VL2054(pΔlacZ), and VL2054(pYGAZH) were suspended in 2 ml of minimal medium (11 g/l $(NH_4)_2SO_4$, 0.4 g/l NaCl, 0.4 g/l $MgSO_4$, 1 g/l $K_2HPO_4$, 1-mg/l $FeSO_4$, 10 mg/l $MnSO_4$, 0.1 mg/l thiamin, 0.5 g/l yeast extract, 40 g/l glucose, 300 mg/l ampicillin, if necessary) in 20-ml test tubes and incubated overnight with aeration at 32° C. 0.2 ml of each night culture was transferred to three 20-ml test tubes with 2 ml of fresh medium for fermentation with or without IPTG and cultivated at 32° C. for 48 or 72 hours on a rotary shaker.

Fermentation medium composition:

| | |
|---|---|
| $(NH_4)_2SO_4$ | 22 g/l |
| NaCl | 0.8 g/l |
| $MgSO_4$ | 0.8 g/l |
| $K_2HPO_4$ | 2 g/l |
| $FeSO_4$ | 20 mg/l |
| $MnSO_4$ | 20 mg/l |
| Thiamin | 0.2 mg/l |
| Yeast extract | 1 g/l |
| $CaCO_3$ | 30 g/l |
| Glucose | 80 g/l |
| Ampicillin | 300 mg/l, if necessary |
| IPTG | 0.5 mM, if necessary |

After cultivation, the plasmid stability and optical absorbance of the medium at 540 nm were determined by conventional methods. The amount of threonine which accumulated in the medium was determined by thin layer chromatography (TLC). The liquid phase composition for TLC was as follows: isopropanol (50 ml), acetone (50 ml), 30% $NH_4OH$ (12 ml), $H_2O$ (8 ml). The results are shown in Table 2. As shown, the presence of the hybrid plasmid pYGAZH improved the amount of threonine accumulation by the threonine producing strain VL2054.

TABLE 2

| VL2054 with plasmid | IPTG | 48 hours | | | 72 hours | | |
|---|---|---|---|---|---|---|---|
| | | $OD_{540}$ | Thr, g/l | Thr/OD | $OD_{540}$ | Thr, g/l | Thr/OD |
| no | − | 19 | 5.2 | 0.27 | 26 | 9.1 | 0.35 |
| | + | 21 | 4.1 | 0.20 | 29 | 7.8 | 0.27 |
| pΔlacZ | − | 20 | 6.4 | 0.32 | 24 | 9.1 | 0.40 |
| | + | 15 | 3.5 | 0.23 | 24 | 7.2 | 0.30 |
| pYGAZH | − | 17 | 5.7 | 0.34 | 24 | 9.7 | 0.40 |
| | + | 21 | 9.8 | 0.47 | 23 | 15.5 | 0.67 |

Example 4

Production of Valine by a Strain with Plasmid pYGAZH

The valine producing strain H-81 was transformed with the pYGAZH plasmid which contains the b2682 and b2683 genes under the control of $P_{lac}$ UV5 promoter. The H-81 strain was deposited in the Russian National Collection of Industrial Microorganisms (VKPM) (Russia 113545, Moscow, 1 Dorozhny proezd, 1) on Jan. 30, 2001 under accession number VKPM B-8066, and converted to an international deposit based on the Budapest Treaty on Feb. 1, 2002.

5 colonies of each H-81 strain, control strain H-81(pΔlacZ), and H-81(pYGAZH) were suspended in 2 ml of minimal medium (18 g/l $(NH_4)_2SO_4$, 1.8 g/l $K_2HPO_4$, 1.2 g/l $MgSO_4$, 0.1 g/l thiamin, 0.5 g/l yeast extract, 60 g/l glucose, 100 mg/l ampicillin, if necessary), in 20-ml test tubes and incubated overnight with aeration at 32° C. 0.2 ml of each night culture was transferred to three 20-ml test tubes with 2 ml of fresh medium for fermentation with or without IPTG and cultivated at 32° C. for 48 or 72 hours on a rotary shaker.

Fermentation medium composition:

| | |
|---|---|
| $(NH_4)_2SO_4$ | 18 g/l, |
| $K_2HPO_4$ | 1.8 g/l, |
| $MgSO_4$ | 1.2 g/l, |
| $CaCO_3$ | 20 g/l, |
| Thiamin | 0.1 mg/l, |
| Glucose | 60 g/l, |
| Ampicillin | 300 mg/l, if necessary |
| IPTG | 0.5 mM, if necessary |

After cultivation, the plasmid stability and optical absorbance of the medium at 540 nm were determined by conventional methods. The amount of valine which accumulated in the medium was determined by TLC. The liquid phase composition for TLC was as follows: isopropanol (80 ml), ethylacetate (80 ml), 30% $NH_4OH$ (15 ml), $H_2O$ (45 ml). The results are shown in Table 3. As shown, the presence of the hybrid plasmid pYGAZH improved the amount of valine which accumulated by the valine producing strain H-81.

TABLE 3

| H-81 with plasmid | IPTG | 48 hours | | | 72 hours | | |
|---|---|---|---|---|---|---|---|
| | | $OD_{540}$ | Val, g/l | Val/OD | $OD_{540}$ | Val, g/l | Val/OD |
| No | − | 34 | 11.6 | 0.34 | 32 | 10.3 | 0.32 |
| | + | 34 | 11.7 | 0.34 | 30 | 10.1 | 0.34 |

TABLE 3-continued

| H-81 with plasmid | IPTG | 48 hours | | | 72 hours | | |
|---|---|---|---|---|---|---|---|
| | | OD$_{540}$ | Val, g/l | Val/OD | OD$_{540}$ | Val, g/l | Val/OD |
| pΔlacZ | − | 34 | 10.5 | 0.31 | 30 | 10.0 | 0.33 |
| | + | 20 | 7.8 | 0.39 | 25 | 9.0 | 0.36 |
| pYGAZH | − | 29 | 10.5 | 0.36 | 31 | 12.8 | 0.41 |
| | + | 22 | 10.8 | 0.49 | 23 | 12.3 | 0.53 |

Reference Example 1

Production of L-proline by an ilvA Deficient L-proline Producer

Cells of wild-type strain *E. coli* K12 (VKPM B-7) were treated with the mutagen N-methyl-N'-nitro-N-nitrosoguanidine (0.1 mg/ml) for 20 min at 37° C., washed and plated on minimal agar medium M9 supplemented with 1.25 mg/ml tryptone, 10 mg/ml L-proline, and 0.05 mg/ml 2,3,5-triphenyltetrazolium chloride. Most colonies which appeared after 3 days of incubation at 37° C. were red. A few colonies which could not oxidize L-proline were white. One of these colonies was used as a parent to obtain mutants resistant to proline analogs (3,4-dehydroxyproline and azetidine-2-carboxylate), which were added to M9 agar medium to a concentration of 2 mg/ml each.

Some of mutants which appeared could produce L-proline. The best L-proline producer, 702, was treated with a P1 bacteriophage grown on cells of the TG1 strain in which the ilvA gene was disrupted by the insertion of the chloramphenicol (Cm) resistance (Cm$^r$) gene. One of Cm resistant transductants, 702ilvA, which turned out to be L-isoleucine auxotrophic, was much more effective at producing L-proline than the L-isoleucine prototrophic parent strain 702 (Table 4). The fermentation medium contained 60 μl glucose, 25 μl ammonium sulfate, 2 μl KH$_2$PO$_4$, 1 g/l MgSO$_4$, 0.1 mg/l thiamine, 50 mg/l L-isoleucine and 25 μl chalk (pH 7.2). Glucose and chalk were sterilized separately. 2 ml of the medium was placed into test tubes, and inoculated with one loop of the tested microorganisms, and the cultivation was carried out at 37° C. for 2 days with shaking.

TABLE 4

| Strain | Phenotype | Accumulation of L-proline (g/l) |
|---|---|---|
| K12 (VKPM B-7) | Wild-type | <0.1 |
| 702 (VKPM B-8011) | Defective L-proline degradation, resistance to proline analogs | 0.5 |
| 702ilvA (VKPM B-8012) | Defective L-proline degradation, resistance to proline analogs, L-isoleucine auxotroph, Cm$^r$ | 8.0 |

The 702 and 702ilvA strains were deposited in the Russian National Collection of Industrial Microorganisms (VKPM) under the accession number VKPM B-8011 and VKPM B-8012, respectively, on Jul. 25, 2000.

Example 5

Production of Proline by a Strain having Plasmid pYGAZH

The proline producing strain *E. coli* 702ilvA was transformed with the plasmid pYGAZH which contains the b2682 and b2683 genes under the control of P$_{lac}$ UV5 promoter.

5 colonies of each 702ilvA strain, control strain 702ilvA (pΔlacZ), and 702ilvA(pYGAZH) were suspended in 2 ml of minimal medium (18 g/l (NH$_4$)$_2$SO$_4$, 1.8 g/l K$_2$HPO$_4$, 1.2 g/l MgSO$_4$, 0.1 mg/l thiamin, 0.5 g/l yeast extract, 60 g/l glucose, 50 mg/l isoleucine, 300 mg/l ampicillin, if necessary) in 20-ml test tubes and incubated overnight with aeration at 32° C. 0.2 ml of each night culture was transferred to three 20-ml test tubes with 2 ml of fresh medium for fermentation with or without IPTG and cultivated at 32° C. for 40 hours with rotary shaker.

Fermentation medium composition:

| (NH$_4$)$_2$SO$_4$ | 18 g/l, |
|---|---|
| K$_2$HPO$_4$ | 1.8 g/l, |
| MgSO$_4$ | 1.2 g/l, |
| CaCO$_3$ | 20 g/l, |
| Thiamin | 0.1 mg/l, |
| Glucose | 60 g/l, |
| Isoleucine | 50 mg/l |
| Ampicillin | 300 mg/l, if necessary |
| IPTG | 0.5 mM, if necessary |

After cultivation, the plasmid stability and optical absorbance of the medium at 540 nm were determined by conventional methods. The amount of proline which accumulated in the medium was determined by TLC. The liquid phase composition for TLC was as follows: ethanol (80 ml), 30% NH$_4$OH (5 ml), H$_2$O (25 ml). The results are shown in Table 5. As shown, the presence of the hybrid plasmid pYGAZH improved the accumulation of proline by the proline producing strain 702ilvA.

TABLE 5

| 702ilvA with plasmid | IPTG | 40 hours | | |
|---|---|---|---|---|
| | | OD$_{540}$ | Pro, g/l | Pro/OD |
| No | − | 25 | 4.0 | 0.16 |
| | + | 23 | 4.1 | 0.18 |
| pΔlacZ | − | 24 | 5.3 | 0.22 |
| | + | 22 | 5.0 | 0.23 |
| pYGAZH | − | 21 | 5.0 | 0.24 |
| | + | 23 | 10.6 | 0.46 |

Reference Example 2

Production of L-leucine by an ilvE Deficient L-leucine Producer

Cells of wild-type strain *E. coli* K12 (VKPM B-7) were treated with the mutagen N-methyl-N'-nitro-N-nitrosoguanidine (0.05 mg/ml) for 20 min at 37° C., washed 4 times with physiological solution and plated on minimal agar medium M9 supplemented with 4.0 mg/ml DL-4-azaleucine. The plates were incubated for 5 days at 37° C. Colonies which appeared on the plates were picked up and purified by streaking on the L-agar plates. One of the mutants which showed resistance to DL-4-azaleucine was used to induce double L-isoleucine and L-valine auxotrophy. Numerous double auxotrophs which require L-isoleucine and L-valine for growth were obtained. Double L-isoleucine and L-valine auxotrophy was shown to be caused by a mutation in the ilvE gene. The best L-leucine producer of the double auxotrophs was selected and shown to be strain 505, which produced 1.8 μl of L-leucine. The fermentation medium contained 60 μl glucose, 25 μl ammonium sulfate, 2 μl KH$_2$PO$_4$, 1 g/l MgSO$_4$, 0.1 mg/l thiamine, 100 mg/l L-isoleucine, 100 mg/l L-valine and 25 μl chalk (pH 7.2). Glucose and chalk were sterilized separately. 2 ml of the medium was placed into test tubes, and inoculated with one loop of the tested microorganisms, and the cultivation was carried out at 37° C. for 2 days with shaking.

The *E. coli* 505 strain was deposited in the Russian National Collection of Industrial Microorganisms (VKPM) (Russia 113545, Moscow, 1 Dorozhny proezd, 1) on May 14, 2001 under accession number VKPM B-8124, and converted to an international deposit under the Budapest Treaty on Feb. 1, 2002.

Example 6

Production of Leucine by a Strain having Plasmid pYGAZH

The leucine producing strain *E. coli* 505 was transformed by the plasmid pYGAZH which contained the b2682 and b2683 genes under the control of the P$_{lac}$ UV5 promoter.

20 colonies of each strain 505, control strain 505(pΔlacZ), and 505(pYGAZH) were transferred by one loop of culture to 20-ml test tubes with L-broth with or without ampicillin, and were incubated overnight with aeration at 32° C. 0.1 ml of each night culture was transferred into the 20-ml test tubes (inner diameter 22 mm), suspended in 2 ml of medium for fermentation with or without IPTG, and cultivated at 32° C. for 72 hours on a rotary shaker.

Fermentation medium composition:

| | |
|---|---|
| (NH$_4$)$_2$SO$_4$ | 15 g/l, |
| K$_2$HPO$_4$ | 1.5 g/l, |
| MgSO$_4$ × 7H$_2$O | 1.0 g/l, |
| CaCO$_3$ | 20 g/l (sterilized separately), |
| Thiamin | 0.1 mg/l, |
| Glucose | 60 g/l (sterilized separately), |
| Isoleucine | 0.3 g/l |
| Valine | 0.3 g/l |
| Ampicillin | 150 mg/l, if necessary |
| IPTG | 0.5 mM, if necessary |

After cultivation, the plasmid stability was determined by a conventional method. The amount of leucine which accumulated in the medium was determined by TLC. The liquid phase composition for TLC was as follows: isopropanol (80 ml), ethylacetate (80 ml), 30% NH$_4$OH (25 ml), H$_2$O (0 ml). The results are shown in Table 6. As shown, the presence of the hybrid plasmid pYGAZH improved the accumulation of leucine by the leucine producing 505 strain.

TABLE 6

| 505 with plasmid | IPTG | 72 hours Leu, g/l |
|---|---|---|
| No | − | 1.8 |
| | + | 2.0 |
| pΔlacZ | − | 1.8 |
| | + | 2.0 |
| pYGAZH | − | 2.0 |
| | + | 2.8 |

Reference Example 3

Production of L-methionine by L-methionine Producer Resistant to Norleucine

The plasmidless threonine and leucine deficient *E. coli* C600 strain was used to derive the following strains. At first, Leu$^+$ variants of *E. coli* C600 strain were obtained by transduction of phage P1 grown on *E. coli* K-12 strain. Then, after treatment with N-methyl-N'-nitro-N-nitrosoguanidine (NTG), the mutant strain 44 was obtained, which is resistant to 8 g/l of L-homoserine. The 44 strain is L-threonine-deficient and resistant to high concentrations of L-homoserine. The 44 strain was deposited in the Russian National Collection of Industrial Microorganisms (VKPM) under the accession number VKPM B-2175.

Then, mutant strains resistant to the methionine analog norleucine were induced from the 44 strain by mutagenesis using NTG. The cells of the night culture grown in L-broth were spun down and resuspended in physiological solution (0.9% NaCl) containing 50 μg/ml of NTG. After 30 min of exposure with NTG at 37° C., the cells were spun down, washed 4 times with physiological solution, and plated on the minimal agar medium M9 containing 0.5 mg/ml of threonine and 2.5 mg/ml or 5.0 mg/ml of norleucine. The plates were incubated for 5 days at 37° C. Colonies which appeared on the plates were purified by streaking on L-agar plates. Strain 218 turned out to be the best L-methionine producer. Test-tube cultivation of the novel 218 strain was performed at 32° C. for 3 days with shaking, and resulted in accumulation in the culture medium of about 1 μl L-methionine. A fermentation medium of minimal medium M9 containing glucose (4%), ammonia sulfate (2.5%), threonine (0.5 μl), calcium carbonate (25 μl) was used. Glucose and chalk were sterilized separately.

The 218 strain was deposited in the Russian National Collection of Industrial Microorganisms (VKPM) under the accession number VKPM B-8125 on May 14, 2001, and converted to an international deposit under the Budapest Treaty on Feb. 1, 2002.

Furthermore, the ppc gene was deleted via P1 phage in the 218 strain, followed by integration of the pycA gene from *Bacillus subtilis* (Russian patent application 99121636). The resulting strain 218pycA lost its resistance to norleucine. Therefore, resistance to norleucine was imparted to the strain again as described above. The best L-methionine producer among obtained strains was strain *E. coli* 73 which produced about 1 g/l of L-methionine under the conditions described above.

The *E. coli* 73 strain was deposited in the Russian National Collection of Industrial Microorganisms (VKPM) (Russia 113545 Moscow 1 Dorozhny proezd, 1) on May 14, 2001 under accession number VKPM B-8126, and converted to an international deposit under the Budapest Treaty on Feb. 1, 2002.

Example 7

Production of Methionine by a Strain having Plasmid pYGAZH

The methionine producing *E. coli* 73 strain was transformed with the plasmid pYGAZH which contains the b2682 and b2683 genes under the control of $P_{lac}$ UV5 promoter.

5 colonies of each strain 73, control stain 73(pΔlacZ), and 73(pYGAZH) were suspended in 2 ml of minimal medium (18 g/l $(NH_4)_2SO_4$, 1.8 g/l $K_2HPO_4$, 1.2 g/l $MgSO_4$, 0.1 mg/l thiamin, 10 g/l yeast extract, 60 g/l glucose, 400 mg/l threonine, 300 mg/l ampicillin, if necessary) in 20-ml test tubes and incubated overnight with aeration at 32° C. 0.2 ml of each night culture was transferred to three 20-ml test tubes with 2 ml of fresh medium for fermentation with or without IPTG, and cultivated at 32° C. for 48 hours on a rotary shaker.

Fermentation medium composition:

| | |
|---|---|
| $(NH_4)_2SO_4$ | 18 g/l, |
| $K_2HPO_4$ | 1.8 g/l, |
| $MgSO_4$ | 1.2 g/l, |
| $CaCO_3$ | 20 g/l, |
| Thiamin | 0.1 mg/l, |
| Glucose | 60 g/l, |
| Threonine | 400 mg/l, |
| Yeast extract | 1.0 g/l, |
| Ampicillin | 300 mg/l, if necessary |
| IPTG | 0.5 mM, if necessary |

After cultivation, the plasmid stability and optical absorbance of the medium at 540 nm were determined by conventional methods. The amount of methionine which accumulated in the medium was determined by TLC. The liquid phase composition for TLC was as follows: isopropanol (80 ml), ethylacetate (80 ml), 30% $NH_4OH$—(15 ml), $H_2O$ (45 ml). The results are shown in Table 7. As shown, the presence of the hybrid plasmid pYGAZH improved the methionine accumulation by the methionine producing 73 strain.

TABLE 7

| 73 with plasmid | IPTG | 48 hours | | |
|---|---|---|---|---|
| | | $OD_{540}$ | Met, g/l | Met/OD |
| No | − | 45 | 0.7 | 0.016 |
| | + | 42 | 1.1 | 0.026 |
| pΔlacZ | − | 45 | 1.0 | 0.022 |
| pYGAZH | − | 48 | 0.9 | 0.019 |
| | + | 46 | 1.3 | 0.028 |

Example 8

Production of Threonine by a Strain having Plasmid pYCHE

The threonine producing VL2054 strain was transformed with the plasmid pYCHE containing the b1242 gene under the control of $P_{lac}$ UV5 promoter. The resulting strain was named VL2054(pYCHE).

5 colonies of each strain VL2054, control strain VL2054 (pΔlacZ), and VL2054(pYCHE) were suspended in 2 ml of minimal medium (11 g/l $(NH_4)_2SO_4$, 0.4 g/l NaCl, 0.4 g/l $MgSO_4$, 1 g/l $K_2HPO_4$, 10 mg/l $FeSO_4$, 10 mg/l $MnSO_4$, 0.1 mg/l thiamin, 0.5 g/l yeast extract, 40 g/l glucose, 300 mg/l ampicillin, if necessary) in 20-ml test tubes and incubated overnight with aeration at 32° C. 0.2 ml of each night culture was transferred to three 20-ml test tubes with 2 ml of fresh medium for fermentation with or without IPTG, and cultivated at 32° C. for 45 hours on a rotary shaker.

Fermentation medium composition:

| | |
|---|---|
| $(NH_4)_2SO_4$ | 22 g/l |
| NaCl | 0.8 g/l |
| $MgSO_4$ | 0.8 g/l |
| $K_2HPO_4$ | 2 g/l |
| $FeSO_4$ | 20 mg/l |
| $MnSO_4$ | 20 mg/l |
| Thiamin | 0.2 mg/l |
| Yeast extract | 1 g/l |
| $CaCO_3$ | 30 g/l |
| Glucose | 80 g/l |
| Ampicilline | 300 mg/l, if necessary |
| IPTG | 0.5 mM, if necessary |

After cultivation, the plasmid stability and optical absorbance of the medium at 540 nm were determined by conventional methods. The amount of threonine which accumulated in the medium was determined by thin layer chromatography (TLC). The liquid phase composition for TLC was as follows: isopropanol (50 ml), acetone (50 ml), 30% $NH_4OH$ (12 ml), $H_2O$ (8 ml). The results are shown in Table 8. As shown, the presence of the hybrid plasmid pYCHE improved the threonine accumulation by the threonine producing strain VL2054.

TABLE 8

| VL2054 with plasmid | IPTG | $OD_{540}$ | Thr, g/l | Thr/OD |
|---|---|---|---|---|
| no | − | 21 | 4.8 | 0.23 |
| | + | 20 | 4.7 | 0.24 |
| pΔlacZ | − | 16 | 4.6 | 0.29 |
| | + | 13 | 3.0 | 0.23 |
| pYCHE | − | 20 | 6.2 | 0.31 |
| | + | 20 | 7.0 | 0.35 |

Example 9

Production of Valine by a Strain having Plasmid pYCHE

The valine producing strain H-81 was transformed with the plasmid pYCHE which contains the b1242 gene under the control of $P_{lac}$ UV5 promoter.

5 colonies of each strain H-81, control strain H-81(pΔlacZ), and H-81(pYCHE) were suspended in 2 ml of minimal medium (18 g/l $(NH_4)_2SO_4$, 1.8 g/l $K_2HPO_4$, 1.2 g/l $MgSO_4$, 0.1 mg/l thiamin, 0.5 g/l yeast extract, 0 g/l glucose, 300 mg/l ampicillin, if necessary) in 20-ml test tubes and incubated overnight with aeration at 32° C. 0.2 ml of each night culture was transferred to three 20-ml test tubes with 2 ml of fresh medium for fermentation with or without IPTG, and cultivated at 32° C. for 45 hours on a rotary shaker.

Fermentation medium composition:

| | |
|---|---|
| $(NH_4)_2SO_4$ | 18 g/l, |
| $K_2HPO_4$ | 1.8 g/l, |
| $MgSO_4$ | 1.2 g/l, |
| $CaCO_3$ | 20 g/l, |

-continued

| | |
|---|---|
| Thiamin | 0.1 mg/l, |
| Glucose | 60 g/l, |
| Ampicilline | 300 mg/l, if necessary |
| IPTG | 0.5 mM, if necessary |

After cultivation, the plasmid stability and optical absorbance of the medium at 540 nm were determined by conventional methods. The amount of valine which accumulated in the medium was determined by TLC. The liquid phase composition for TLC was as follows: 80 ml isopropanol, 80 ml ethylacetate, 15 ml 30% NH$_4$OH, 45 ml H$_2$O. The results are shown in Table 9. As shown, the presence of the hybrid plasmid pYCHE improved the valine accumulation by the valine producing strain H-81.

TABLE 9

| H-81 with plasmid | IPTG | OD$_{540}$ | Val, g/l | Val/OD |
|---|---|---|---|---|
| no | − | 34 | 11.6 | 0.34 |
| | + | 34 | 11.7 | 0.34 |
| pΔlacZ | − | 34 | 10.5 | 0.31 |
| | + | 20 | 7.8 | 0.39 |
| pYCHE | − | 32 | 14.0 | 0.44 |
| | + | 30 | 13.9 | 0.46 |

Example 10

Production of Arginine by a Strain having Plasmid pYHGN

The arginine producing strain 382 was transformed with the plasmid pYHGN which contains the b3434 gene under the control of the P$_{lac}$ UV5 promoter. The 382 strain was deposited in the Russian National Collection of Industrial Microorganisms (VKPM) (Russia 113545, Moscow, 1 Dorozhny proezd, 1) on Apr. 10, 2000 under accession number VKPM B-7926.

5 colonies of each strain 382, control strain 382(pΔlacZ), and 382(pYHGN) were suspended in 2 ml of minimal medium (25.0 g/l (NH$_4$)$_2$SO$_4$, 2.0 g/l K$_2$HPO$_4$, 1.0 g/l MgSO$_4$ 7H$_2$O, 0.1 mg/l thiamin, 5 g/l yeast extract, 60 g/l glucose, 100 mg/l ampicillin, if necessary) in 20-ml test tubes and incubated overnight with aeration at 32° C. 0.2 ml of each night culture was transferred to three 20-ml test tubes with 2 ml of fresh medium for fermentation with or without IPTG, and cultivated at 32° C. for 72 hours on a rotary shaker.

Fermentation medium composition:

| | |
|---|---|
| (NH$_4$)$_2$SO$_4$ | 25 g/l, |
| K$_2$HPO$_4$ | 2.0 g/l, |
| MgSO$_4$ 7H$_2$O | 1.0 g/l, |
| Thiamin | 0.2 mg/l, |
| Yeast extract | 5 g/l |
| Glucose | 60 g/l, |
| CaCO$_3$ | 20 g/l |
| Ampicilline | 100 mg/l, if necessary |
| IPTG | 0.5 mM, if necessary |

After cultivation, the plasmid stability and optical absorbance of the medium at 540 nm were determined by conventional methods. The amount of arginine which accumulated in the medium was determined by TLC. The liquid phase composition for TLC was as follows: 80 ml isopropanol, 40 ml ethylacetate, 15 ml 30% NH$_4$OH, 50 ml H$_2$O. The results are shown in Table 10. As shown, the presence of the hybrid plasmid pYHGN improved the arginine accumulation by the arginine producing strain 382.

TABLE 10

| E. coli 382 with plasmid | IPTG | OD$_{540}$ | Arg, g/l | Arg/OD |
|---|---|---|---|---|
| No | − | 20 | 8.5 | 0.43 |
| | + | 22 | 6.7 | 0.31 |
| pΔlacZ | − | 28 | 6.3 | 0.23 |
| | + | 26 | 5.4 | 0.21 |
| pYHGN | − | 24 | 5.8 | 0.24 |
| | + | 26 | 9.3 | 0.36 |

Example 11

Production of Proline by a Strain having Plasmid pYHGN

The proline producing strain E. coli 702ilvA was transformed with the plasmid pYHGN which contains the b3434 gene under the control of the P$_{lac}$ UV5 promoter.

5 colonies of each strain 702ilvA, control strain 702ilvA (pΔlacZ), and 702ilvA(pYHGN) were suspended in 2 ml of minimal medium (18 g/l (NH$_4$)$_2$SO$_4$, 1.8 g/l K$_2$HPO$_4$, 1.2 g/l MgSO$_4$, 0.1 mg/l thiamin, 0.5 g/l yeast extract, 60 g/l glucose, 50 mg/l isoleucine, 300 mg/l ampicillin, if necessary) in 20-ml test tubes and incubated overnight with aeration at 32° C. 0.2 ml of each night culture was transferred to three 20-ml test tubes with 2 ml of fresh medium for fermentation with or without IPTG, and cultivated at 32° C. for 40 hours on a rotary shaker.

Fermentation medium composition:

| | |
|---|---|
| (NH$_4$)$_2$SO$_4$ | 18 g/l, |
| K$_2$HPO$_4$ | 1.8 g/l, |
| MgSO$_4$ | 1.2 g/l, |
| CaCO$_3$ | 20 g/l, |
| Thiamin | 0.1 mg/l, |
| Glucose | 60 g/l, |
| Isoleucine | 50 mg/l |
| Ampicilline | 300 mg/l, if necessary |
| IPTG | 0.5 mM, if necessary |

After cultivation, the plasmid stability and optical absorbance of the medium at 540 nm were determined by conventional methods. The amount of proline which accumulated in the medium was determined by TLC. The liquid phase composition for TLC was as follows: 80 ml ethanol, 5 ml 30% NH$_4$OH, 25 ml H$_2$O. The results are shown in Table 11. As shown, the presence of the hybrid plasmid pYHGN improved the proline accumulation by the proline producing strain 702ilvA.

TABLE 11

| 702ilvA with plasmid | | 40 hours | | |
|---|---|---|---|---|
| | IPTG | OD$_{540}$ | Pro, g/l | Pro/OD |
| No | − | 25 | 4.0 | 0.16 |
| | + | 23 | 4.1 | 0.18 |

TABLE 11-continued

| 702ilvA with plasmid | IPTG | 40 hours | | |
|---|---|---|---|---|
| | | OD$_{540}$ | Pro, g/l | Pro/OD |
| PΔlacZ | − | 24 | 5.3 | 0.22 |
| | + | 22 | 5.0 | 0.23 |
| pYHGN | − | 24 | 5.9 | 0.25 |
| | + | 17 | 7.1 | 0.42 |

Modifications and Other Embodiments

Various modification and variations of the described products, compositions, and methods as well as the concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the biochemical, chemical, chemical engineering, molecular biological, medical, or pharmacological arts or related fields are intended to be within the scope of the following claims.

INCORPORATION BY REFERENCE

Each document, patent application or patent publication cited by or referred to in this disclosure is incorporated by reference in its entirety. Any patent document to which this application claims priority is also incorporated by reference in its entirety. Specifically, priority documents Russian Patent Application No. 2001103865, filed Feb. 13, 2001; Russian Patent Application No. 2001104998, filed Feb. 26, 2001; Russian Patent Application No. 2001104999, filed Feb. 26, 2001; Russian Patent Application 2001117632, filed Jun. 28, 2001; and Russian Patent Application No. 2001117633, filed Jun. 28, 2001 are hereby incorporated by reference.

What is claimed is:

1. An isolated L-amino acid producing bacterium belonging to the genus *Escherichia*, wherein the bacterium has increased expression of a gene encoding a protein selected from the group consisting of:
   (A) a protein comprising the amino acid sequence in SEQ ID NO:16; and
   (B) a protein comprising the amino acid sequence of SEQ ID NO:16 except that a total of between 1 and 5 amino acids are deleted, substituted, inserted, or added,
   wherein the expression of said proteins is increased by transformation of said bacterium with the gene coding for said protein, or by placing said gene under the control of a potent promoter.

2. The bacterium according to the claim 1, wherein the transformation is performed with a multicopy vector.

3. The bacterium according to claim 1, wherein the protein (A) is encoded by the polynucleotide which has the nucleotide sequence of SEQ ID NO:15.

4. The bacterium according to claim 1, wherein the protein (B) is encoded by a polynucleotide which hybridizes with a sequence which is complementary to the nucleotide sequence of SEQ ID NO:15 under conditions comprising washing in 1×SSC and 0.1% SDS at 60° C.

5. A method for producing an L-amino acid comprising:
   A) cultivating the bacterium according to claim 1 in a culture medium, and
   B) collecting the L-amino acid from the culture medium.

6. The method according to claim 5, wherein the L-amino acid is L-arginine.

7. The method according to claim 6, wherein the bacterium has been modified so that the bacterium has enhanced expression of the arginine regulon as compared to a non-modified bacterium.

8. The method according to claim 5, wherein the L-amino acid is L-proline.

9. The method according to claim 8, wherein the bacterium has been modified so that the bacterium has enhanced expression of the genes for proline biosynthesis as compared to a non-modified bacterium.

10. A method for producing an L-amino acid comprising:
    A) cultivating the bacterium according to claim 2 in a culture medium, and
    B) collecting the L-amino acid from the culture medium.

11. The method according to claim 10, wherein the L-amino acid is L-arginine.

12. The method according to claim 11, wherein the bacterium has been modified so that the bacterium has enhanced expression of the arginine regulon as compared to a non-modified bacterium.

13. The method according to claim 10, wherein the L-amino acid is L-proline.

14. The method according to claim 13, wherein the bacterium has been modified so that the bacterium has enhanced expression of genes for proline biosynthesis as compared to a non-modified bacterium.

15. The bacterium of claim 1, wherein said protien imparts increased resistance to an L-amino acid selected from the group consisting of DL-o-methylserine, 6-diazo-5-oxo-L-norleucine, and DL-β-hydroxy-norvaline,
    and wherein said bacterium has increased sensitivity to S-(2-aminoethyl)cysteine.

* * * * *

UNITED STATES PATENT AND TRADEMARK OFFICE
CERTIFICATE OF CORRECTION

PATENT NO. : 7,618,804 B2
APPLICATION NO. : 12/120409
DATED : November 17, 2009
INVENTOR(S) : Tabolina et al.

It is certified that error appears in the above-identified patent and that said Letters Patent is hereby corrected as shown below:

Column 38, lines 27-32 should read

15. The bacterium of claim 1, wherein said protein imparts increased resistance to an L-amino acid selected from the group consisting of DL-o-methylserine, 6-diazo-5-oxo-L-norleucine, and DL-.beta.-hydroxy-norvaline, and wherein said bacterium has increased sensitivity to S-(2-aminoethyl)cysteine.

Signed and Sealed this

Twenty-third Day of March, 2010

David J. Kappos
*Director of the United States Patent and Trademark Office*

SEQUENCE LISTING

```
<160> NUMBER OF SEQ ID NOS: 16

<210> SEQ ID NO 1
<211> LENGTH: 26
<212> TYPE: DNA
<213> ORGANISM: Artificial Sequence
<220> FEATURE:
<223> OTHER INFORMATION: Synthetic DNA

<400> SEQUENCE: 1
ggtctagaca atcgttaagc gtacac                                          26

<210> SEQ ID NO 2
<211> LENGTH: 26
<212> TYPE: DNA
<213> ORGANISM: Artificial Sequence
<220> FEATURE:
<223> OTHER INFORMATION: Synthetic DNA

<400> SEQUENCE: 2
ccggatccga tatagtaacg acagtg                                          26

<210> SEQ ID NO 3
<211> LENGTH: 738
<212> TYPE: DNA
<213> ORGANISM: Escherichia coli
<220> FEATURE:
<221> NAME/KEY: CDS
<222> LOCATION: (1)..(735)

<400> SEQUENCE: 3 atg gaa agc cct act cca cag cct gct cct ggt tcg gcg acc ttc atg    48
Met Glu Ser Pro Thr Pro Gln Pro Ala Pro Gly Ser Ala Thr Phe Met
1               5                   10                  15 gaa gga tgc aaa gac agt tta ccg att gtt att agt tat att ccg gtg    96
Glu Gly Cys Lys Asp Ser Leu Pro Ile Val Ile Ser Tyr Ile Pro Val
            20                  25                  30 gcc ttt gcg ttc ggt ctg aat gcg acc cgt ctg gga ttc tct cct ctc   144
Ala Phe Ala Phe Gly Leu Asn Ala Thr Arg Leu Gly Phe Ser Pro Leu
        35                  40                  45 gaa agc gtt ttt ttc tcc tgc atc att tat gca ggc gcg agc cag ttc   192
```

```
Glu Ser Val Phe Phe Ser Cys Ile Ile Tyr Ala Gly Ala Ser Gln Phe
 50                  55                  60 gtc att acc gcg atg ctg gca gcc ggg agt agt ttg tgg att gct gca      240
Val Ile Thr Ala Met Leu Ala Ala Gly Ser Ser Leu Trp Ile Ala Ala
 65                  70                  75                  80 ctg acc gtc atg gca atg gat gtt cgc cat gtg ttg tat ggc ccg tca      288
Leu Thr Val Met Ala Met Asp Val Arg His Val Leu Tyr Gly Pro Ser
 85                  90                  95 ctg cgt agc cgt att att cag cgt ctg caa aaa tcg aaa acc gcc ctg      336
Leu Arg Ser Arg Ile Ile Gln Arg Leu Gln Lys Ser Lys Thr Ala Leu
100                 105                 110 tgg gcg ttt ggc ctg acg gat gag gtt ttt gcc gcc gca acc gca aaa      384
Trp Ala Phe Gly Leu Thr Asp Glu Val Phe Ala Ala Ala Thr Ala Lys
115                 120                 125 ctg gta cgc aat aat cgc cgc tgg agc gag aac tgg atg atc ggc att      432
Leu Val Arg Asn Asn Arg Arg Trp Ser Glu Asn Trp Met Ile Gly Ile
130                 135                 140 gcc ttc agt tca tgg tca tcg tgg gta ttt ggt acg gta ata ggg gca      480
Ala Phe Ser Ser Trp Ser Ser Trp Val Phe Gly Thr Val Ile Gly Ala
145                 150                 155                 160 ttc tcc ggc agc ggc ttg ctg caa ggt tat ccc gcc gtt gaa gct gca      528
Phe Ser Gly Ser Gly Leu Leu Gln Gly Tyr Pro Ala Val Glu Ala Ala
165                 170                 175 tta ggt ttt atg ctt ccg gca ctc ttt atg agt ttc ctg ctc gcc tct      576
Leu Gly Phe Met Leu Pro Ala Leu Phe Met Ser Phe Leu Leu Ala Ser
180                 185                 190 ttc cag cgc aaa caa tct ctt tgc gtt acc gca gcg tta gtt ggt gcc      624
Phe Gln Arg Lys Gln Ser Leu Cys Val Thr Ala Ala Leu Val Gly Ala
195                 200                 205 ctt gca ggc gta acg cta ttt tct att ccc gtc gcc att ctg gca ggc      672
Leu Ala Gly Val Thr Leu Phe Ser Ile Pro Val Ala Ile Leu Ala Gly
210                 215                 220 att gtc tgt ggc tgc ctc act gcg tta atc cag gca ttc tgg caa gga      720
Ile Val Cys Gly Cys Leu Thr Ala Leu Ile Gln Ala Phe Trp Gln Gly
225                 230                 235                 240 gcg ccc gat gag cta tga                                               738
Ala Pro Asp Glu Leu
245

<210> SEQ ID NO 4
<211> LENGTH: 245
<212> TYPE: PRT
<213> ORGANISM: Escherichia coli

<400> SEQUENCE: 4

Met Glu Ser Pro Thr Pro Gln Pro Ala Pro Gly Ser Ala Thr Phe Met
 1               5                  10                  15

Glu Gly Cys Lys Asp Ser Leu Pro Ile Val Ile Ser Tyr Ile Pro Val
 20                  25                  30

Ala Phe Ala Phe Gly Leu Asn Ala Thr Arg Leu Gly Phe Ser Pro Leu
 35                  40                  45

Glu Ser Val Phe Phe Ser Cys Ile Ile Tyr Ala Gly Ala Ser Gln Phe
 50                  55                  60

Val Ile Thr Ala Met Leu Ala Ala Gly Ser Ser Leu Trp Ile Ala Ala
 65                  70                  75                  80

Leu Thr Val Met Ala Met Asp Val Arg His Val Leu Tyr Gly Pro Ser
 85                  90                  95

Leu Arg Ser Arg Ile Ile Gln Arg Leu Gln Lys Ser Lys Thr Ala Leu
100                 105                 110
```

```
Trp Ala Phe Gly Leu Thr Asp Glu Val Phe Ala Ala Thr Ala Lys
115                 120                 125

Leu Val Arg Asn Asn Arg Arg Trp Ser Glu Asn Trp Met Ile Gly Ile
130                 135                 140

Ala Phe Ser Ser Trp Ser Ser Trp Val Phe Gly Thr Val Ile Gly Ala
145                 150                 155                 160

Phe Ser Gly Ser Gly Leu Leu Gln Gly Tyr Pro Ala Val Glu Ala Ala
165                 170                 175

Leu Gly Phe Met Leu Pro Ala Leu Phe Met Ser Phe Leu Leu Ala Ser
180                 185                 190

Phe Gln Arg Lys Gln Ser Leu Cys Val Thr Ala Ala Leu Val Gly Ala
195                 200                 205

Leu Ala Gly Val Thr Leu Phe Ser Ile Pro Val Ala Ile Leu Ala Gly
210                 215                 220

Ile Val Cys Gly Cys Leu Thr Ala Leu Ile Gln Ala Phe Trp Gln Gly
225                 230                 235                 240

Ala Pro Asp Glu Leu
245

<210> SEQ ID NO 5
<211> LENGTH: 336
<212> TYPE: DNA
<213> ORGANISM: Escherichia coli
<220> FEATURE:
<221> NAME/KEY: CDS
<222> LOCATION: (1)..(333)

<400> SEQUENCE: 5 atg agc tat gag gtt ctg ctg ctt ggg tta cta gtt ggc gtg gcg aat      48
Met Ser Tyr Glu Val Leu Leu Leu Gly Leu Leu Val Gly Val Ala Asn
1               5                   10                  15 tat tgc ttc cgc tat ttg ccg ctg cgt ctg cgt gtg ggt aat gcc cgc      96
Tyr Cys Phe Arg Tyr Leu Pro Leu Arg Leu Arg Val Gly Asn Ala Arg
                20                  25                  30 cca acc aaa cgt ggc gcg gta ggt att ttg ctc gac acc att ggc atc     144
Pro Thr Lys Arg Gly Ala Val Gly Ile Leu Leu Asp Thr Ile Gly Ile
            35                  40                  45 gcc tcg ata tgc gct ctg ctg gtt gtc tct acc gca cca gaa gtg atg     192
Ala Ser Ile Cys Ala Leu Leu Val Val Ser Thr Ala Pro Glu Val Met
        50                  55                  60 cac gat aca cgc cgt ttc gtg ccc acg ctg gtc ggc ttc gcg gta ctg     240
His Asp Thr Arg Arg Phe Val Pro Thr Leu Val Gly Phe Ala Val Leu
    65                  70                  75                  80 ggt gcc agt ttc tat aaa aca cgc agc att atc atc cca aca ctg ctt     288
Gly Ala Ser Phe Tyr Lys Thr Arg Ser Ile Ile Ile Pro Thr Leu Leu
                85                  90                  95 agt gcg ctg gcc tat ggg ctc gcc tgg aaa gtg atg gcg att ata taa     336
Ser Ala Leu Ala Tyr Gly Leu Ala Trp Lys Val Met Ala Ile Ile
            100                 105                 110

<210> SEQ ID NO 6
<211> LENGTH: 111
<212> TYPE: PRT
<213> ORGANISM: Escherichia coli

<400> SEQUENCE: 6

Met Ser Tyr Glu Val Leu Leu Leu Gly Leu Leu Val Gly Val Ala Asn
1               5                   10                  15

Tyr Cys Phe Arg Tyr Leu Pro Leu Arg Leu Arg Val Gly Asn Ala Arg
```

```
                20                  25                  30
Pro Thr Lys Arg Gly Ala Val Gly Ile Leu Leu Asp Thr Ile Gly Ile
 35                  40                  45

Ala Ser Ile Cys Ala Leu Leu Val Val Ser Thr Ala Pro Glu Val Met
 50                  55                  60

His Asp Thr Arg Arg Phe Val Pro Thr Leu Val Gly Phe Ala Val Leu
 65                  70                  75                  80

Gly Ala Ser Phe Tyr Lys Thr Arg Ser Ile Ile Pro Thr Leu Leu
 85                  90                  95

Ser Ala Leu Ala Tyr Gly Leu Ala Trp Lys Val Met Ala Ile Ile
100                 105                 110

<210> SEQ ID NO 7
<211> LENGTH: 37
<212> TYPE: DNA
<213> ORGANISM: Artificial Sequence
<220> FEATURE:
<223> OTHER INFORMATION: Synthetic DNA

<400> SEQUENCE: 7
cctttggtac cagatctgcg ggcagtgagc gcaacgc                              37

<210> SEQ ID NO 8
<211> LENGTH: 34
<212> TYPE: DNA
<213> ORGANISM: Artificial Sequence
<220> FEATURE:
<223> OTHER INFORMATION: Synthetic DNA

<400> SEQUENCE: 8
ctgtttctag atcctgtgtg aaattgttat ccgc                                 34

<210> SEQ ID NO 9
<211> LENGTH: 28
<212> TYPE: DNA
<213> ORGANISM: Artificial Sequence
<220> FEATURE:
<223> OTHER INFORMATION: Synthetic DNA

<400> SEQUENCE: 9
ggtctagata tggctaacat tatccggc                                        28

<210> SEQ ID NO 10
<211> LENGTH: 28
<212> TYPE: DNA
<213> ORGANISM: Artificial Sequence
<220> FEATURE:
<223> OTHER INFORMATION: Synthetic DNA

<400> SEQUENCE: 10
ccggatccaa acggagcatg gcagctcc                                        28

<210> SEQ ID NO 11
<211> LENGTH: 648
<212> TYPE: DNA
<213> ORGANISM: Escherichia coli
<220> FEATURE:
<221> NAME/KEY: CDS
<222> LOCATION: (1)..(645)

<400> SEQUENCE: 11 gtg att cag acc ttt ttt gat ttt ccc gtt tac ttc aaa ttt ttc atc      48
Val Ile Gln Thr Phe Phe Asp Phe Pro Val Tyr Phe Lys Phe Phe Ile
 1               5                  10                  15
```

```
ggg tta ttt gcg ctg gtc aac ccg gta ggg att att ccc gtc ttt atc      96
Gly Leu Phe Ala Leu Val Asn Pro Val Gly Ile Ile Pro Val Phe Ile
 20                  25                  30 agc atg acc agt tat cag aca gcg gca gcg cga aac aaa act aac ctt     144
Ser Met Thr Ser Tyr Gln Thr Ala Ala Ala Arg Asn Lys Thr Asn Leu
 35                  40                  45 aca gcc aac ctg tct gtg gcc att atc ttg tgg atc tcg ctt ttt ctc     192
Thr Ala Asn Leu Ser Val Ala Ile Ile Leu Trp Ile Ser Leu Phe Leu
 50                  55                  60 ggc gac acg att cta caa ctt ttt ggt ata tca att gat tcg ttc cgt     240
Gly Asp Thr Ile Leu Gln Leu Phe Gly Ile Ser Ile Asp Ser Phe Arg
 65                  70                  75                  80 atc gcc ggg ggt atc ctg gtg gtg aca ata gcg atg tcg atg atc agc     288
Ile Ala Gly Gly Ile Leu Val Val Thr Ile Ala Met Ser Met Ile Ser
 85                  90                  95 ggc aag ctt ggc gag gat aaa cag aac aag caa gaa aaa tca gaa acc     336
Gly Lys Leu Gly Glu Asp Lys Gln Asn Lys Gln Glu Lys Ser Glu Thr
100                 105                 110 gcg gta cgt gaa agc att ggt gtg gtg cca ctg gcg ttg ccg ttg atg     384
Ala Val Arg Glu Ser Ile Gly Val Val Pro Leu Ala Leu Pro Leu Met
115                 120                 125 gcg ggg cca ggg gcg atc agt tct acc atc gtc tgg ggt acg cgt tat     432
Ala Gly Pro Gly Ala Ile Ser Ser Thr Ile Val Trp Gly Thr Arg Tyr
130                 135                 140 cac agc att agc tat ctg ttt ggt ttc ttt gtg gct att gca ttg ttc     480
His Ser Ile Ser Tyr Leu Phe Gly Phe Phe Val Ala Ile Ala Leu Phe
145                 150                 155                 160 gct tta tgt tgt tgg gga ttg ttc cgc atg gca ccg tgg ctg gta cgg     528
Ala Leu Cys Cys Trp Gly Leu Phe Arg Met Ala Pro Trp Leu Val Arg
165                 170                 175 gtt tta cgc cag acc ggc atc aac gtg att acg cgt att atg ggg cta     576
Val Leu Arg Gln Thr Gly Ile Asn Val Ile Thr Arg Ile Met Gly Leu
180                 185                 190 ttg ctg atg gca ttg ggg att gaa ttt atc gtt act ggt att aag ggg     624
Leu Leu Met Ala Leu Gly Ile Glu Phe Ile Val Thr Gly Ile Lys Gly
195                 200                 205 att ttc ccc ggc ctg ctt aat taa                                     648
Ile Phe Pro Gly Leu Leu Asn
210                 215

<210> SEQ ID NO 12
<211> LENGTH: 215
<212> TYPE: PRT
<213> ORGANISM: Escherichia coli

<400> SEQUENCE: 12

Val Ile Gln Thr Phe Phe Asp Phe Pro Val Tyr Phe Lys Phe Phe Ile
 1                   5                  10                  15

Gly Leu Phe Ala Leu Val Asn Pro Val Gly Ile Ile Pro Val Phe Ile
 20                  25                  30

Ser Met Thr Ser Tyr Gln Thr Ala Ala Ala Arg Asn Lys Thr Asn Leu
 35                  40                  45

Thr Ala Asn Leu Ser Val Ala Ile Ile Leu Trp Ile Ser Leu Phe Leu
 50                  55                  60

Gly Asp Thr Ile Leu Gln Leu Phe Gly Ile Ser Ile Asp Ser Phe Arg
 65                  70                  75                  80

Ile Ala Gly Gly Ile Leu Val Val Thr Ile Ala Met Ser Met Ile Ser
 85                  90                  95
```

```
Gly Lys Leu Gly Glu Asp Lys Gln Asn Lys Gln Glu Lys Ser Glu Thr
100                 105                 110

Ala Val Arg Glu Ser Ile Gly Val Val Pro Leu Ala Leu Pro Leu Met
115                 120                 125

Ala Gly Pro Gly Ala Ile Ser Ser Thr Ile Val Trp Gly Thr Arg Tyr
130                 135                 140

His Ser Ile Ser Tyr Leu Phe Gly Phe Phe Val Ala Ile Ala Leu Phe
145                 150                 155                 160

Ala Leu Cys Cys Trp Gly Leu Phe Arg Met Ala Pro Trp Leu Val Arg
        165                 170                 175

Val Leu Arg Gln Thr Gly Ile Asn Val Ile Thr Arg Ile Met Gly Leu
180                 185                 190

Leu Leu Met Ala Leu Gly Ile Glu Phe Ile Val Thr Gly Ile Lys Gly
195                 200                 205

Ile Phe Pro Gly Leu Leu Asn
210                 215
```

<210> SEQ ID NO 13
<211> LENGTH: 28
<212> TYPE: DNA
<213> ORGANISM: Artificial Sequence
<220> FEATURE:
<223> OTHER INFORMATION: Synthetic DNA

<400> SEQUENCE: 13
ggtctagagt ccgcggcaat tatcaggg                                     28

<210> SEQ ID NO 14
<211> LENGTH: 29
<212> TYPE: DNA
<213> ORGANISM: Artificial Sequence
<220> FEATURE:
<223> OTHER INFORMATION: Synthetic DNA

<400> SEQUENCE: 14
ccagatctgg tagttgtgac gctaccggg                                    29

<210> SEQ ID NO 15
<211> LENGTH: 594
<212> TYPE: DNA
<213> ORGANISM: Escherichia coli
<220> FEATURE:
<221> NAME/KEY: CDS
<222> LOCATION: (1)..(591)

<400> SEQUENCE: 15

```
atg aat gaa atc att tct gca gca gtt tta ttg atc ctg att atg gat      48
Met Asn Glu Ile Ile Ser Ala Ala Val Leu Leu Ile Leu Ile Met Asp
1               5                   10                  15 ccg ctc gga aac cta cct att ttc atg tcc gta ctg aaa cat act gaa      96
Pro Leu Gly Asn Leu Pro Ile Phe Met Ser Val Leu Lys His Thr Glu
            20                  25                  30 ccg aaa aga cgg cgg gca atc atg gtg cga gag ttg ctt att gct ctc     144
Pro Lys Arg Arg Arg Ala Ile Met Val Arg Glu Leu Leu Ile Ala Leu
        35                  40                  45 ctg gtg atg ctg gtg ttc ctg ttt gcg ggt gag aaa att ctg gca ttt     192
Leu Val Met Leu Val Phe Leu Phe Ala Gly Glu Lys Ile Leu Ala Phe
    50                  55                  60 ctt agc cta cga gca gaa acc gtc tcc att tct ggc ggc atc att ctg     240
Leu Ser Leu Arg Ala Glu Thr Val Ser Ile Ser Gly Gly Ile Ile Leu
65                  70                  75                  80
```

```
ttt ctg atc gcc att aaa atg att ttc ccc agc gct tca gga aat agc     288
Phe Leu Ile Ala Ile Lys Met Ile Phe Pro Ser Ala Ser Gly Asn Ser
 85                  90                  95 agc ggg ctt ccg gca ggt gaa gag cca ttt atc gtg ccg ttg gca att     336
Ser Gly Leu Pro Ala Gly Glu Glu Pro Phe Ile Val Pro Leu Ala Ile
100                 105                 110 ccg tta gtc gcc ggg ccg act att ctc gcc acg ctg atg ttg ttg tct     384
Pro Leu Val Ala Gly Pro Thr Ile Leu Ala Thr Leu Met Leu Leu Ser
115                 120                 125 cat cag tac ccg aat cag atg ggg cat ctg gtg att gct ctg ctg ctg     432
His Gln Tyr Pro Asn Gln Met Gly His Leu Val Ile Ala Leu Leu Leu
130                 135                 140 gcc tgg ggc ggc acc ttt gtc atc ctg cta cag tct tcg cta ttt tta     480
Ala Trp Gly Gly Thr Phe Val Ile Leu Leu Gln Ser Ser Leu Phe Leu
145                 150                 155                 160 cgt ctg ctg ggc gag aaa ggg gtg aac gca ctt gaa cgc ctg atg gga     528
Arg Leu Leu Gly Glu Lys Gly Val Asn Ala Leu Glu Arg Leu Met Gly
165                 170                 175 ttg att ctg gtg atg atg gca acc cag atg ttc ctc gac ggc att cga     576
Leu Ile Leu Val Met Met Ala Thr Gln Met Phe Leu Asp Gly Ile Arg
180                 185                 190 atg tgg atg aag ggg taa                                             594
Met Trp Met Lys Gly
195

<210> SEQ ID NO 16
<211> LENGTH: 197
<212> TYPE: PRT
<213> ORGANISM: Escherichia coli

<400> SEQUENCE: 16

Met Asn Glu Ile Ile Ser Ala Ala Val Leu Ile Leu Ile Met Asp
  1               5                  10                  15

Pro Leu Gly Asn Leu Pro Ile Phe Met Ser Val Leu Lys His Thr Glu
 20                  25                  30

Pro Lys Arg Arg Arg Ala Ile Met Val Arg Glu Leu Leu Ile Ala Leu
 35                  40                  45

Leu Val Met Leu Val Phe Leu Phe Ala Gly Glu Lys Ile Leu Ala Phe
 50                  55                  60

Leu Ser Leu Arg Ala Glu Thr Val Ser Ile Ser Gly Gly Ile Ile Leu
 65                  70                  75                  80

Phe Leu Ile Ala Ile Lys Met Ile Phe Pro Ser Ala Ser Gly Asn Ser
 85                  90                  95

Ser Gly Leu Pro Ala Gly Glu Glu Pro Phe Ile Val Pro Leu Ala Ile
100                 105                 110

Pro Leu Val Ala Gly Pro Thr Ile Leu Ala Thr Leu Met Leu Leu Ser
115                 120                 125

His Gln Tyr Pro Asn Gln Met Gly His Leu Val Ile Ala Leu Leu Leu
130                 135                 140

Ala Trp Gly Gly Thr Phe Val Ile Leu Leu Gln Ser Ser Leu Phe Leu
145                 150                 155                 160

Arg Leu Leu Gly Glu Lys Gly Val Asn Ala Leu Glu Arg Leu Met Gly
165                 170                 175

Leu Ile Leu Val Met Met Ala Thr Gln Met Phe Leu Asp Gly Ile Arg
180                 185                 190

Met Trp Met Lys Gly
195
```